(12) United States Patent
Tschaplinski et al.

(10) Patent No.: US 11,725,215 B2
(45) Date of Patent: Aug. 15, 2023

(54) METHODS FOR CONTROLLING CELL WALL BIOSYNTHESIS AND GENETICALLY MODIFIED PLANTS

(71) Applicant: UT-Battelle, LLC, Oak Ridge, TN (US)

(72) Inventors: Timothy J. Tschaplinski, Oak Ridge, TN (US); Daniel A. Jacobson, Oak Ridge, TN (US); David Kainer, Knoxville, TN (US); Deborah A. Weighill, Somerville, MA (US); Anna K. Furches, Knoxville, TN (US)

(73) Assignees: UT-Battelle, LLC, Oak Ridge, TN (US); University of Tennessee Research Foundation, Knoxville, TN (US)

( * ) Notice: Subject to any disclaimer, the term of this patent is extended or adjusted under 35 U.S.C. 154(b) by 552 days.

(21) Appl. No.: 16/590,993

(22) Filed: Oct. 2, 2019

(65) Prior Publication Data
US 2020/0102571 A1 Apr. 2, 2020

Related U.S. Application Data

(60) Provisional application No. 62/739,961, filed on Oct. 2, 2018.

(51) Int. Cl.
*C12N 15/82* (2006.01)
*D21H 11/00* (2006.01)
*C12P 7/06* (2006.01)

(52) U.S. Cl.
CPC ..... *C12N 15/8262* (2013.01); *C12N 15/8213* (2013.01); *C12N 15/8218* (2013.01); *C12P 7/06* (2013.01); *D21H 11/00* (2013.01)

(58) Field of Classification Search
None
See application file for complete search history.

(56) References Cited

U.S. PATENT DOCUMENTS 9,617,557 B2 * 4/2017 Reuzeau ............ C12N 15/8261

OTHER PUBLICATIONS

Omidbakhshfard et al, 2018, PLoS Genet, 14:1-31.*
Fan et al, 2015, Sci. Rep., 5:1-7.*
Cao et al, 2016, Frontiers in Plant Sci., 7:1-14.*
Sannigrahi et al, 2010, Biofuels, Bioprod, Bioref, 4:209-226.*
Franco-Zorilla, J.M., et al., "DNA-binding specificities of plant transcription factors and their potential to define target genes", PNAS, Feb. 11, 2014, pp. 2367-2372, vol. 111, No. 6.

Furches, A., et al., "Finding New Cell Wall Regulatory Genes in Populus trichocarpa Using Multiple Lines of Evidence", Frontiers in Plant Science Oct. 2019, Received Feb. 15, 2019, Accepted Sep. 9, 2019, Published Oct. 8, 2019, 17 pages, vol. 10, Article 1249.
Gonzalez, N., et al., "Leaf size control: complex coordination of cell division and expansion", Trends in Plant Science, Jun. 2012, pp. 332-340, vol. 17, No. 6.
Joshi, R., et al., "Transcription Factors and Plants Response to Drought Stress: Current Understanding and Future Directions", Frontiers in Plant Science Jul. 2016, Received Apr. 10, 2016, Accepted Jun. 30, 2016, Published Jul. 14, 2016, 15 pages, vol. 7, Article 1029.
Kim, J.-H., et al., "Regulation of plant growth and development by the Growth-Regulating Factor and Grf-Nteracting Factor duo", Journal of Experimental Botany 2015, Received Apr. 14, 2015, Revised Jun. 16, 2015, Accepted Jun. 22, 2015, pp. 6093-6107, vol. 66, No. 20.
Kim, J.-S., et al., "Arabidopsis Growth-Regulating FACTOR7 Functions as a Transcriptional Repressor of Abscisic Acid- and Osmotic Stress-Responsive Genes, Including DREB2A", The Plant Cell Aug. 2012, Received May 25, 2012, revised Jul. 27, 2012, accepted Aug. 9, 2012, published Aug. 31, 2012, pp. 3393-3405, vol. 24.
Kuijt, S.J.H., et al., "Interaction between the Growth-Regulating Factor and KNOTTED1-Like Homeobox Families of Transcription Factors", Plant Physiology Apr. 2014, Received Jun. 13, 2013, accepted Feb. 13, 2014, published Feb. 14, 2014, pp. 1952-1966, vol. 164.
Mukherjee, K., et al., "A Comprehensive Classification and Evolutionary Analysis of Plant Homeobox Genes", Mol. Biol. Evol, Accepted Aug. 20, 2009, Sep. 4, 2009, p. 2/15-2794, 26(12).
Park, M.Y., et al., "Overexpression of AtMYB52 Confers ABA Hypersensitivity and Drought Tolerance", Molecules and Cells May 31, 2011, Received Dec. 3, 2010, revised Jan. 22, 2011, accepted Feb. 7, 2011, published online Mar. 9, 2011, pp. 447-454, 31.
Wai, C.M., "Cell wall metabolism and hexose allocation contribute to biomass accumulation in high yielding extreme segregants of a Saccharum interspecific F2 population", BMC Genomics (2017), Received Jan. 31, 2017, Accepted Oct. 5, 2017, Published online Oct. 11, 2017, 14 pages, 18:773.
Zhong, R., et al., "A Battery of Transcription Factors Involved in the Regulation of Secondary Cell Wall Biosynthesis n Arabidopsis", The Plant Cell, Oct. 2008, pp. 2763-2782, vol. 20.

* cited by examiner

*Primary Examiner* — Jason Deveau Rosen
(74) *Attorney, Agent, or Firm* — Scully, Scott, Murphy & Presser, P.C.

(57) ABSTRACT

The present disclosure provides methods of producing plants with preferred levels of cell wall biosynthesis; and uses of such plants. The inventors have identified that the GFR9, CCoAOMT and MYB41 genes are major regulators of the cell wall biosynthesis pathway. Plants with modulated cell wall biosynthesis, based on modulation of the expression or activity of the GFR9, CCoAOMT and MYB41 genes, have divergent uses including pulp and paper production, and bioproduct production.

16 Claims, 5 Drawing Sheets
(5 of 5 Drawing Sheet(s) Filed in Color)
Specification includes a Sequence Listing.

METHODS FOR CONTROLLING CELL WALL BIOSYNTHESIS AND GENETICALLY MODIFIED PLANTS

CROSS REFERENCE TO RELATED APPLICATION

This application claims the benefit of priority from U.S. Provisional Application No. 62/739,961, filed Oct. 2, 2018, the contents of which are incorporated herein by reference.

STATEMENT REGARDING FEDERALLY SPONSORED RESEARCH OR DEVELOPMENT

This invention was made with government support under Prime Contract No. DE-AC05-00OR22725 awarded by the U.S. Department of Energy. The government has certain rights in the invention.

INCORPORATION BY REFERENCE OF SEQUENCE LISTING

The Sequence Listing in an ASCII text file, named as 37757_4227_1_SequenceListing.txt of 15 KB, created on Sep. 26, 2019, and submitted to the United States Patent and Trademark Office via EFS-Web, is incorporated herein by reference.

BACKGROUND

The biosynthesis and regulation of the plant cell wall has been the subject of a large body of research due to the industrial importance of lignocellulosic biomass, as well as the role of the cell wall in the function of other plant biological systems such as hormone signaling, stress response and inter-cellular transport. For industrially cultivated genera, such as *Populus*, the main cell wall constituents (cellulose, lignin, hemicellulose, pectin) provide the immediate feedstock for downstream products including biofuel, lumber, paper and advanced lignin products (Sannigrahi, P. et al. (2010). *Biofuels, Bioprod. Biorefining* 4, 209-226; Porth, I. et al. (2013). *New Phytol.*, 200, 727-742.). Therefore, there is great interest in understanding the mechanisms that regulate the biosynthesis and modification of the cell wall, both from a yield and composition perspective.

A great variety of biopolymers are synthesized and incorporated into the primary and secondary cell wall, often in response to biotic and abiotic stress, nutrient availability, and developmental and temporal switches, all of which govern the macro-scale form of the plant. A highly complex network of genetic regulation has evolved to control the rate of biosynthesis of cell wall polymers, their intrinsic monomer composition, their transport to and subsequent deposition in the cell wall, and the expansion of the wall under changing intra cellular conditions. In the model plant *Arabidopsis thaliana*, Bischoff et al. (2010) estimated that over 1,000 genes encode proteins related to the cell wall, while Cai et al. (2014) predicted a number closer to 3,000 based on clustering of gene co-expression (Bischoff et al. 2010, *Plant Physiol.* 153, 590-602; Cai et al. 2014, *PLoS One* 9, e95176). Furthermore, Taylor-Teeples et al. (2015) tested a library of 1,664 transcription factors in *A. thaliana* for interaction with the promoter regions of cell wall biosynthesis genes and found 413 such interactions in root vascular tissue alone (Taylor-Teeples et al. 2015, *Nature* 517, 571).

Due to poplar's status as a model tree and its importance for lignocellulosic products, many studies have investigated the regulatory network of the cell wall and its components specifically in *Populus* species or in multiple genera in combination with Populus (Porth et al. 2013, *New Phytol.* 200, 727-742; Ko et al. 2014, *Ann. Bot.* 114, 1099-1107; Wang et al. 2014, *Sci. Rep.* 4, 5054; Zhong & Ye 2014, *Plant Cell Physiol.* 56, 195-214; Ohtani et al. 2011, *Plant J.* 67, 499-512; Lin et al. 2017, *Proc. Natl. Acad. Sci.*, 201714422; Yu et al. 2013, *Tree Physiol.* 34, 1289-1300; Lu et al. 2013, *Proc. Natl. Acad. Sci.* 110, 10848-10853; Puzey et al. 2012, *PloS one*, 7(3 e33034; Shi et al. 2017, *Planta* 245, 927-938).

Many studies, such as those referenced above, focus either on characterizing *Populus* homologs of genes that have been shown to have an effect on the cell wall chemistry or plant growth traits in mutant *Arabidopsis* lines, or perhaps were shown to be differentially expressed in comparisons of low and high growth genotypes. However, exploring the regulatory network controlling the cell wall in order to find new functional mechanisms is a challenging task due to the number of genes involved, extensive functional redundancy, and the multitude of transcriptional feedback loops. Consider the view that complex quantitative traits are actually "omnigenic" (Boyle et al. 2017, *Cell* 169, 1177-1186) such that virtually any expressed gene has a non-zero effect on the core biosynthetic genes at the transcriptional, post-transcriptional, post-translational, signaling or protein-protein interaction levels. Huge numbers of loci across the entire genome contribute small portions of the trait heritability, be it directly or indirectly, rather than a few core genes in biosynthetic pathways explaining the major portion of heritability. Under this omnigenic model, network-theory-based methods provide a particularly elegant approach for mining omics datasets for regulatory relationships. Any biological entity (SNP, gene, protein, metabolite etc.) can be modeled as a node, and any relationship between those entities (association, co-expression, correlation, binding) can be modeled as an edge.

The network approach has been used in several studies of cell wall regulation to date, often focusing on finding clusters of genes that co-express with each other in certain tissues, thus finding putative functional units or networks. For example, Cai et al. (2014) performed co-expression network clustering in *Populus* and found major sub-clusters enriched for primary cell wall or secondary cell wall genes (Cai et al. 2014, *PLoS One* 9, e95176). Taylor-Teeples et al. (2015) produced networks based on *A. thaliana* transcription factors and their target binding sites, providing an expanded view of the multi-tiered regulatory system with respect to secondary cell wall (SCW) biosynthesis and xylem development. Yang et al. (2011) used 121 *A. thaliana* anchor cell wall genes obtained from text mining followed by co-expression neighbor analysis to identify 694 *A. thaliana* genes and their 817 *Populus* orthologs as candidate genes for involvement in cell wall functions (Yang et al. 2011, *Plant Sci.* 181, 675-687). Alejandro et al. (2012) identified the ABCG29 genes as transporting monolignol to the cell wall in *A. thaliana* by first analyzing co-expression networks followed by expression and functional analyses (Alejandro et al. 2012, *Curr. Biol.* 22, 1207-1212). These methods often produce a large list of candidate genes but with little more to support their involvement in cell wall regulation than the clustering or enrichment evidence.

Multi-omic approaches have also been performed, which include more data types in identification of candidate genes. Porth et al. (2013) used a network-based multi-omic approach to find relationships between SNP, gene expression, and wood phenotype data from *P. trichocarpa*. They constructed six phenotypic-centric networks to identify genes that most influenced the expression of their related phenotype. From this study, they were able to identify candidate genes potentially related to cell wall biogenesis. Mizrachi et al. (2017, *Proc. Natl. Acad. Sci.* 114, 1195-1200) used a network-based approach to integrate known gene interactions and eQTN data in the form of a connectivity matrix with gene expression data through matrix multiplication in order to identify genes involved in lignin related traits.

BRIEF SUMMARY OF THE DISCLOSURE

In one aspect, this disclosure provides a genetically modified plant, the genetic modification comprising (a) inactivation of an endogenous Growth Factor 9 transcription factor (GRF9), a paralog of GRF9 or a homolog thereof; or (b) overexpression of a gene that is regulated by GRF9; wherein the genetic modification results in an increase in cell wall biosynthesis.

Another aspect of the disclosure is directed to a method comprising (a) inactivating in a plant an endogenous Growth Factor 9 transcription factor (GRF9), a paralog of GRF9 or a homolog thereof; or (b) overexpres sing in a plant a gene that is regulated by GRF9; thereby resulting in an increase in cell wall biosynthesis.

In some embodiments, the inactivation of GRF9 is achieved by introducing a nucleic acid inhibitor of GRF9 the plant. In some embodiments, the nucleic acid inhibitor is selected from the group consisting of an antisense RNA, a small interfering RNA, an RNAi, a microRNA, an artificial microRNA, and a ribozyme.

In some embodiments, the inactivation of GRF9 is achieved by a genome editing method selected from the group consisting of CRISPR/Cas system, Cre/Lox system, TALEN system, ZFNs system and homologous recombination. In some embodiments, the CRISPR-mediated genome editing comprises introducing into the plant a first nucleic acid encoding a Cas9 nuclease, a second nucleic acid comprising a guide RNA (gRNA), wherein said gRNA is specific to GRF9.

In some embodiments, the gene that is regulated by GRF9 is selected from the group consisting of caffeoyl-CoA O-methyltransferase (CCoAOMT) and MYB41, and wherein the overexpression in the plant is achieved by an exogenous nucleic acid comprising the selected gene.

In some embodiments, the plant is a monocot or a dicot. In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea,* and *Zoysia.*

In some embodiments, the plant is *Populus trichocarpa,* and the inactivation of an endogenous GRF9 transcription factor comprises inactivation of both PtGRF9a and PtGRF9b in the plant.

Another aspect of the disclosure is directed to a method for production of pulp or paper, comprising producing pulp or paper from the genetically modified plant cell or plant tissue of the instant disclosure.

Another aspect of the disclosure is directed to a method for producing a bioproduct, comprising subjecting the genetically modified plant cell or plant tissue of the instant disclosure to a bioproduct conversion process.

In some embodiments, the bioproduct is selected from the group consisting of a bioenergy product, a biomaterial, a biopharmaceutical and a biocosmetics. In some embodiments, the bioenergy product is selected from the group consisting of ethanol, butanol and isobutanol. In a specific embodiment, the bioenergy product is ethanol and the bioproduct conversion process is an ethanol fermentation process. In some embodiments, the bioproduct is selected from the group consisting of ethanol, butanol, isobutanol, biodiesel, biogas, bioplastics, biofoams, biorubber, biocomposites, and biofibres.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

Figure 1:
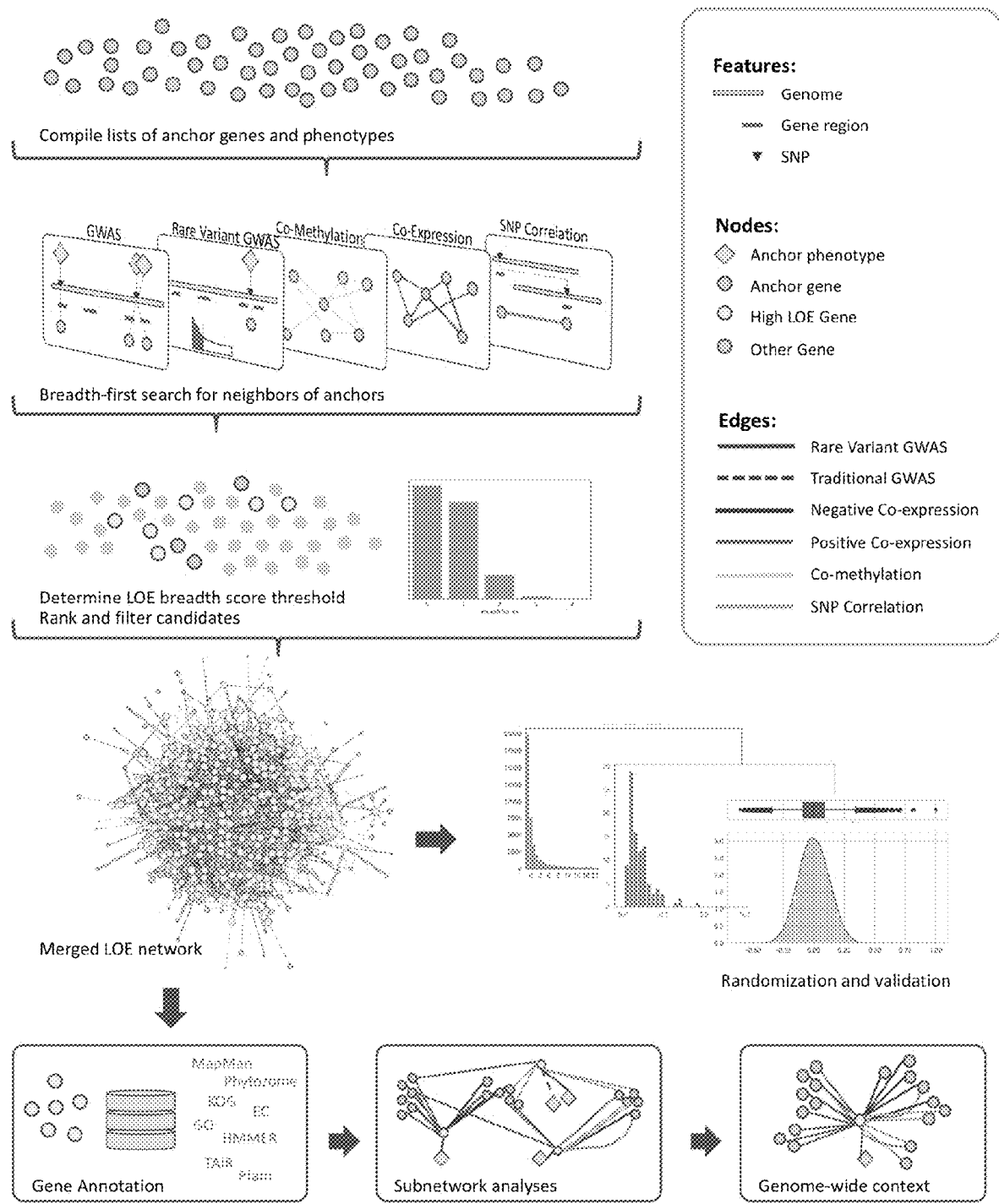
FIG. 1. Overview of the method for identifying new candidate genes involved in cell wall regulation through data layering and calculation of LOE scores.

As used herein, the term "about" refers to a variation within approximately ±10% from a given value.

As used herein, "allelic variants" are alternative forms of the same gene or genetic locus. Each allelic variant has a distinct nucleic acid sequence at the locus of interest. For example, the inventors have discovered two allelic variants of the GFR9 gene, the nucleic acid sequences of which differ from each other by at least one nucleotide. An allelic variant of GFR9 can encode the amino acid sequence as set forth in SEQ ID NO: 1, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 1. Another allelic variant of GFR9 can encode the amino acid sequence as set forth in SEQ ID NO: 2, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 2. An allelic variant of CCoAOMT can encode the amino acid sequence as set forth in SEQ ID NO: 3, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 3. Another allelic variant of CCoAOMT can encode the amino acid sequence as set forth in SEQ ID NO: 4, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 4. An allelic variant of MYB41 can encode the amino acid sequence as set forth in SEQ ID NO: 5, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO: 5. Sequence identity refers to the percent of exact matches between the amino acids of two sequences which are being compared. Where one allelic variant encodes a truncated protein relative to the protein encoded by another allelic variant, percent identity can be determined by comparing the amino acid sequences of the variants along the length of the shorter protein.

This disclosure also provides homologs of the polypeptide encoded by GRF9 gene. An GRF9 homolog can be a homolog, ortholog or variant of the polypeptide having the amino acid sequence set forth in SEQ ID NO: 1. For example, an GRF9 homolog can have an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in SEQ ID NO:1.

In some embodiments, a homolog of GRF9 is a functional homolog. A functional homolog is a polypeptide that has sequence similarity to SEQ ID NO: 1 and that carries out one or more of the biochemical or physiological function(s) of the polypeptide of SEQ ID NO: 1. A functional homolog may be a natural occurring polypeptide and the sequence similarity may be due to convergent or divergent evolutionary events. As such, functional homologs are sometimes designated in the literature as homologs or orthologs or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cell wall-modulating polypeptide or by combining domains from the coding sequences for different naturally-occurring cell wall-modulating polypeptides ("domain swapping"). The term "functional homolog" can also be applied to the nucleic acid that encodes a functionally homologous polypeptide.

An "altered level of gene expression" refers to a measurable or observable change in the level of expression of a transcript of a gene, or the amount of the encoded polypeptide, relative to a control plant or plant cell under the same conditions (e.g., as measured through a suitable assay such as quantitative RT-PCR, a Northern blot, a Western blot, RNA-Seq, Mass spectrometry or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state. An altered level of gene expression of a particular gene can be 5%, 10%, 20%, 30%, 40%, 50%, 60%, 70%, 80%, 90%, 95%, 99%, 100% or more relative to the expression of the gene in a control plant or plant cell under the same conditions.

As used herein, the term "bioproduct" refers to products made from biological materials. In some embodiments, "bioproducts" include bioenergy products (e.g., liquid fuels (such as ethanol and biodiesel), solid biomass for combustion to generate heat and power, and gaseous fuel (such as biogas and syngas) which can be used to generate heat and power). In some embodiments, "bioproducts" include biomaterials (e.g., bioplastics from plant oils and sugars, biofoams and biorubber from plant oils and latex, biocomposites manufactured from agricultural (e.g., hemp, flax, kenaf) and forestry biofibres, used, for example, in the production of automobile door panels and parts). In some embodiments, "bioproducts" include biochemicals (e.g., industrial materials including, but not limited to, basic and specialty chemicals and resins, including paints, lubricants and solvents), biopharmaceuticals (e.g., natural source medicinal compounds), and biocosmetics (e.g., soaps, body creams, shampoos, lotions, herbal extracts)).

The term "control plant" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

As used herein, the term "CRISPR" refers to a RNA-guided endonuclease comprising a nuclease, such as Cas9, and a guide RNA that directs cleavage of the DNA by hybridizing to a recognition site in the genomic DNA.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase. The term "expression" also refers to the process of converting genetic information into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "homolog" means a gene related to a second gene by descent from a common ancestral DNA sequence, therefore, the corresponding polynucleotide/polypeptide has a certain degree of homology, that is to say sequence identity (at least 40%, 60%, 65%, 66%, 68%, 70%, 75%, 80%, 86%, 88%, 90%, 92%, 95%, 97% or 99% sequence identity). The term "paralog" refers to a homolog in the same species that evolved by genetic duplication of a common ancestral gene. In some embodiments, a paralog of a gene has at least 40%, 60%, 65%, 66%, 68%, 70%, 75%, 80%, 86%, 88%, 90%, 92%, 95%, 97% or 99% sequence identity to the original gene.

As used herein, the term "nucleic acid" has its general meaning in the art and refers to refers to a coding or non coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e. nuclear or mitochondrial).

A "nucleic acid inhibitor" is a nucleic acid that can reduce or prevent expression or activity of a target gene. For example, an inhibitor of expression of GRF9 gene can reduce or eliminate transcription and/or translation of the GRF9 gene product, thus reducing GRF9 gene protein expression.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a carrier of genetic information, such as a plasmid, phage or cosmid, into which another DNA segment may be inserted so as to transport or deliver the inserted segment. In some embodiments, a vector is capable of replication when associated with the proper control elements. In other embodiments a vector is incorporated into a target genome and may replicate together with the genome. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif), Stratagene (La Jolla, Calif.) and Invitrogen/Life Technologies (Carlsbad, Calif.).

General Description

The inventors of the present disclosure have determined that the Growth Factor 9 transcription factor (GRF9), and some genes regulated by GRF9, regulate the cell wall biosynthesis pathway. Disclosed herein are methods of controlling cell wall biosynthesis in a plant by altering the expression of the GRF9 gene or a gene regulated by GRF9 in said plant. Also disclosed herein are transgenic plants wherein the expression of the GRF9 gene is or a gene regulated by GRF9 is altered.

In some embodiments, the alteration of the GRF9 gene is inactivation of the GRF9 gene in the plant.

In some embodiments, the gene regulated by GRF9 is selected from the group consisting of caffeoyl-CoA 0-methyltransferase (CCoAOMT) or MYB41. In some embodiments, the alteration of the gene regulated by GRF9 is overexpression of the gene in the plant.

Plants

As used herein, the term "plant" includes whole plants, plant tissues and plant cells. The methods and compositions of the present disclosure can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea*, Miscanthus hybrid (*Miscanthu sx giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba, trichocarpa* and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

Inactivation of the GFR9 Gene

The present inventors have discovered that inactivation of the GRF9 gene in a plant results in increased cell wall biosynthesis, which is desirable to improve plant biomass.

In some embodiments, the GRF9 gene is inactivated in a plant using targeted genome editing techniques. Targeted genome editing (also known as genome engineering) has emerged as an alternative to classical plant breeding and transgenic (Genetically Modified Organism—GMO) methods to improve crop plants. Available methods for targeted genome editing include the CRISPR/Cas system, zinc finger nucleases (ZFNs), and TAL effector nucleases (TALENs). ZFNs are reviewed in Carroll, D. (*Genetics*, 188.4 (2011): 773-782), and TALENs are reviewed in Zhang et al. (*Plant Physiology*, 161.1 (2013): 20-27), which are incorporated herein in their entirety.

CRISPR/Cas system is a method based on the bacterial type II CRISPR (clustered regularly interspaced short palindromic repeats)/Cas (CRISPR-associated) immune system. The CRISPR/Cas system allows targeted cleavage of genomic DNA guided by a customizable small noncoding RNA, resulting in gene modifications by both non-homologous end joining (NHEJ) and homology-directed repair (HDR) mechanisms. CRISPR-Cas and similar gene targeting systems are well known in the art with reagents and protocols readily available. Exemplary genome editing protocols are described in Jennifer Doudna, and Prashant Mali, "*CRISPR-Cas: A Laboratory Manual*" (2016) (CSHL *Press*, ISBN: 978-1-621821-30-4) and Ran, F. Ann, et al. (*Nature Protocols* (2013), 8 (11): 2281-2308). Belhaj et al. (*Plant Methods*, 2013, 9:39) summarizes and discusses applications of the CRISPR/Cas technology in plants and is incorporated herein in its entirety.

In some embodiments, the inactivation of the GRF9 gene is achieved by nucleic acid inhibitors of expression of the GRF9 gene.

A number of nucleic acid-based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit GRF9 gene expression in plants. Suitable inhibitors include full-length nucleic acids of allelic variants of GRF9 gene, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid fragment from a gene to be repressed is cloned and operably linked to a heterologous regulatory region and a transcription termination sequence so that the antisense strand of RNA is transcribed. The recombinant vector is then transformed into plants, as described below and the antisense strand of RNA is produced. The nucleic acid fragment needs not be the entire sequence of the gene to be repressed, but typically is substantially complementary to at least a portion of the sense strand of the gene to be repressed. By "substantially complementary" it is meant that the nucleic acid fragment is capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, 8%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a heterologous regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite or an alkyl phosphotriester backbone.

Overexpression Genes Regulated by GRF9

The present inventors have discovered that alteration of some genes regulated by GRF9 in a plant results in altered cell wall biosynthesis.

In some embodiments, the gene regulated by GRF9 is caffeoyl-CoA O-methyltransferase (CCoAOMT). In some embodiments, the gene regulated by GRF9 is MYB41. In some embodiments, the alteration of the gene regulated by GRF9 is overexpression of the gene in the plant.

In some embodiments, overexpression of a gene regulated by GRF9 is achieved by an exogenous nucleic acid with a regulatory region operably linked to a nucleic acid encoding a gene regulated by GRF9, where a tissue of a plant produced from the plant cell has an increased cell wall biosynthesis compared to the cell wall in tissue of a control plant that does not comprise the nucleic acid.

Expression Vectors for Modulating the Activity of GFR9 Gene or Genes Regulated by GFR9

The polynucleotides and expression vectors described herein can be used to increase or inhibit expression of the GFR9 gene or genes regulated by the GFR9 gene.

The vectors provided herein can include origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag- tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab IR promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis* SUC2 sucrose-H+ symporter promoter (Truernit et al., *Planta*, 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate:CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell*, 3(10):1051-1061 (1991)), the Commelina yellow mottle virus (CoYMV) promoter (Medberry et al., *Plant Cell*, 4(2):185-192 (1992)) and the rice tungro bacilliform virus (RTBV) promoter (Dai et al., *PNAS*, 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a vector, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Techniques for introducing nucleic acids (inhibitors and expression vectors) into monocotyledonous and dicotyledonous plants are known in the art and include, without limitation, Agrobacterium-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., *Plant Cell Rep.* V19:304-310 (2000); Chang and Yang, *Bot. Bull. Acad. Sin.*, V37:35-40 (1996) and Han et al., *Biotechnology in Agriculture and Forestry*, V44:291 (ed. by Y. P. S. Bajaj), Springer-Vernag, (1999).

Genetically-modified (Transgenic) Plants/Plant Species/Plant Cells

Also disclosed herein are plants and plant cells genetically modified by introduction of the disclosed nucleic acid inhibitors, CRISPR constructs and expression vectors.

A plant or plant cell used in methods of the invention contains a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous CCoAOMT or MYB41 gene allelic variant whose expression has not previously been confirmed in particular recipient cells.

Initial and immediate application of the expression of GFR9 gene allelic variants can be made in the bioenergy crops Populus and switchgrass, but the application can be extended to other bioenergy crops such as corn, other sources of lignocellulosic biomass and other model plants e.g., *Salix, Miscanthus*, rice and *Medicago*.

For example, the polynucleotides and vectors described herein can be used to transform a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, miscanthus, oat, rice, rye, ryegrass, sorghum, sudangrass, sugarcane, sweet corn, switchgrass, turf grasses, timothy and wheat. Gymnosperms such as fir, pine and spruce can also be suitable.

The methods and compositions can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus hybrid (Miscanthus x giganteus), Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

Methods of Modulating Plant Phenotypes Using Expression Vector Modulators of GFR9 or Genes Regulated by the GFR9 Gene.

This disclosure provides methods of altering cell wall biosynthesis, comprising introducing into a plant cell an exogenous nucleic acid with a regulatory region operably linked to a nucleic acid encoding a gene regulated by GFR9 or an allelic variant of said gene, where a tissue of a plant produced from the plant cell has an altered cell wall compared to the cell wall in tissue of a control plant that does not comprise the nucleic acid. In some embodiments, the gene regulated by GFR9 is CCoAOMT or MYB41.

In one embodiment, the exogenous nucleic acid is an expression vector encoding the polypeptide of a gene regulated by GFR9 that leads to increased cell wall biosynthesis. An example of such an expression vector is an expression vector comprising the CCoAOMT gene allelic variant encoding SEQ ID NO: 3. A second example of such an expression vector is an expression vector comprising the CCoAOMT gene allelic variant encoding SEQ ID NO: 4. A third example of such an expression vector is an expression vector comprising the MYB41 gene allelic variant encoding SEQ ID NO: 5. Expression of such a vector in a plant or plant cell would lead to a increase in cell wall biosynthesis in that plant or plant cell.

In one example, the coding sequence of a gene regulated by GFR9 or its allelic variant is amplified from either genomic DNA or cDNA by PCR. The DNA fragments are then subcloned into an expression construct. In this example, a construct is made by first digesting pSAT4A-DEST-n(1-

174)EYFP-N1 (ABRC stock #CD3-1080) and pSAT5-DEST-c(175-end)EYFP-C1(B) (ABRC stock #CD3-1097) (Citovsky V. et al., *J Mol Biol* 362:1120-1131 (2006)) with NdeI and BglII, then ligating the 1.1 kb fragment of the first construct and 4.4 kb fragment of the second one, followed by subcloning of the coding sequence of a gene regulated by GFR9 or its allelic variant into the construct to create the expression vector.

Methods of Use of Transgenic Plants

Disclosed herein are methods of using transgenic plants with reduced or inhibited expression or activity of the GFR9 gene in a bioproduct conversion process, for instance, for producing a bioenergy product, a biomaterial, a biopharmaceutical and a biocosmetics. Also disclosed herein are methods of using transgenic plants with increased expression or activity of the caffeoyl-CoA O-methyltransferase (CCoAOMT) gene in a bioproduct conversion process, for instance, for producing a bioenergy product, a biomaterial, a biopharmaceutical and a biocosmetics. Also disclosed herein are methods of using transgenic plants with increased expression or activity of the MYB41 gene in a bioproduct conversion process, for instance, for producing a bioenergy product, a biomaterial, a biopharmaceutical and a biocosmetics.

In some embodiments, the bioenergy product is selected from the group consisting of ethanol, butanol, isobutanol, biodiesel, and biogas. In some embodiments, the biomaterial is selected from the group consisting of bioplastics, biofoams, biorubber, biocomposites, and biofibres. In some embodiments, the biopharmaceutical product is a natural source medicinal compound. In some embodiments, the biocosmetics is selected from the group consisting of soaps, body creams, shampoos, lotions, and herbal extracts made using the transgenic plants described in this application.

Further disclosed herein are improved methods of producing biofuel from cellulosic biomass, by using plants with reduced or inhibited expression or activity of the GFR9 gene in biofuel production processes.

Methods of pretreatment and saccharification of biomass to fermentable sugars, followed by fermentation of the sugars to ethanol, are known in the art. Ethanol fermentation process, also called alcoholic fermentation process, is a biological process which converts sugars such as glucose, fructose, and sucrose into cellular energy, producing ethanol and carbon dioxide as a side-effect. In some embodiments this conversion takes places in the absence of oxygen.

The overall chemical formula for ethanol/alcohol fermentation is:

$$C_6H_{12}O_6 \rightarrow 2C_2H_5OH + 2CO_2$$

Additionally disclosed are methods of producing paper and pulp, by using plants with reduced or inhibited expression or activity of the GFR9 gene in paper or pulp production processes, as known in the art. Further disclosed are pulp and paper products produced by this method, using plants with increased expression of the caffeoyl-CoA O-methyltransferase (CCoAOMT) gene or the MYB41 gene.

Another embodiment provides a plant, a plant cell or a plant tissue with improved cell wall biosynthesis comprising a loss of function mutation in GFR9 gene, or an overexpression of caffeoyl-CoA O-methyltransferase (CCoAOMT) gene or MYB41 gene.

Articles of Manufacture

The materials and methods described herein are useful for modifying biomass characteristics. "Biomass" refers to any cellulosic or lignocellulosic raw material and includes materials containing cellulose, and optionally further containing hemicellulose, lignin, starch, oligosaccharides and/or monosaccharides. The term "cellulosic" refers to a composition containing cellulose. The term "lignocellulosic" refers to a composition containing both lignin and cellulose. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

The invention also relates to the use of the pulp obtained from the disclosed genetically modified plants in the production of cellulose-based products, for example, in the paper industry, or for the production of cardboard. Pulp, produced using plants which have been genetically modified to have decreased expression of the GFR9 gene or to have overexpression of caffeoyl-CoA O-methyltransferase (CCoAOMT) or MYB41, and therefore also have increased cell wall biosynthesis, can be used as a building material and in particular as output material for pressed chipboard, fiberboard of medium density, or as filler material.

Example 1: Materials and Methods

This study makes use of various data accumulated for *P. trichocarpa*, which has been subject to multiple investigations to date and provides a multi-omics resource in a model tree. This data includes SNP data from a GWAS population, foliar metabolites measured in this GWAS population, and DNA methylation data across 10 different *P. trichocarpa* tissues (Vining et al. 2012, *BMC Genomics* 13, 27) as well as the *P. trichocarpa* gene expression atlas on Phytozome (Goodstein et al. 2011, *Nucleic Acids Res.* 40, D1178--D1186). Each data set available was considered as a separate layer for this study, and integrated though the use of Lines of Evidence (LOE) scores. Below, the various layers are described as well as the network analysis methods used to merge layers and identify genes with high connectivity to cell wall systems.

Phenotypes

The inventors made use of metabolite data previously assayed from leaf tissue and analyzed using GC-MS. Details canbe found in references (Weighill et al. 2018, *Front. Energy Res.* 6, 30; Y. Li et al. 2012, *J. Plant Physiol.* 213, 1-15; Tschaplinski et al. 2012, *Biotechnol. Biofuels* 5, 71). The inventors also obtained individual mass to charge (m/z) peaks from pyMBMS analysis of xylem tissue, as many m/z masses represent lignocellulosic components. To prevent spurious associations the inventors examined each phenotype for the presence of outliers using Median Absolute Deviation (MAD). If a sample's phenotype was more than 6 MADs from the population median then it was removed from the GWAS for that phenotype.

Genotypes

Variant data was obtained from the Bioenergy GWAS website and SNPs were filtered to the top 90% tranche (PASS SNPs) and call rate >=0.5 using Plink (Purcell et al. 2007) and VCFtools (Danecek et al. 2011, *Bioinformatics* 27, 2156-2158).

Genome Wide Association layer

The inventors performed GWAS using a linear mixed model (LMM) that estimates the effect of each SNP while accounting for population structure and cryptic relatedness between samples. The tested SNPs excluded those with MAF <0.01, and those with a population call rate below 0.75. Separately the inventors used LD pruning on the main set of SNPs to produce an independent set of SNPs for calculation of the genomic relationship matrix (K) for inclusion in the LMM. SNP effects for each phenotype were estimated with EMMAX and the resulting P-values were FDR corrected.

Rare Variant GWAS Layer

While the GWAS Linear Mixed Model (LMM) tested common and less common SNPs (MAF>0.01) individually for significance, rarer SNPs were tested regionally in a joint fashion. The inventors grouped together rare SNPs (MAF<0.01) located within a given gene, or in the gene's 2 kb upstream and downstream flanking regions, as a region defined by that gene. The inventors then used RVtest (Zhan et al. 2016, *Bioinformatics* 32, 1423-1426) to apply the Sequence Kernel Association Test (SKAT) to each of the 41,335 regions defined from *P. trichocarpa* v3.0 annotations. SKAT tests each SNP in the region individually with an LMM and then forms a combined region score where each component SNP is weighted according to its MAF. Weights were drawn from a beta distribution with default shape parameters (1, 25). This produced a single P-value for the significance of association of each region, which the inventors corrected for multiple testing with an FDR of 0.1.

Co-Expression Layer

A *P. trichocarpa* gene co-expression network was constructed as described in (Weighill et al. 2018, *Front. Energy Res.* 6, 30). RNA-seq reads from the JGI Plant Gene Atlas project were obtained, trimmed using Skewer (Jiang et al. 2014, *BMC Bioinformatics* 15, 182), aligned to the version 3.0 *P. trichocarpa* reference (Tuskan et al. 2006, *Science* 313, 1596-1604) using Star (Dobin et al. 2013, *Bioinformatics* 29, 15-21), and TPM (transcripts per million) values calculated for each gene and each sample. The inventors then calculated the Spearman correlation coefficient between the expression profiles of all pairs of genes using the mcxarray package (Van Dongen 2008, *SIAM J. Matrix Anal. Appl.* 30, 121-141) available from Markov Cluster (MCL) Algorithm website. An absolute threshold of 0.85 was applied in order to keep only those gene-gene pairs with strong co-expression.

Co-Methylation Layer

A *P. trichocarpa* gene co-methylation network was constructed as described in (Weighill et al. 2018, *Front. Energy Res.* 6, 30). MEDIP-Seq reads from the study by Vining et al. (2012) mapped to the version 3 genome assembly of *P. trichocarpa* were obtained from Phytozome (Vining et al. 2012, *BMC Genomics* 13, 27; Goodstein et al. 2011, *Nucleic Acids Res.* 40, D1178-D1186). The number of reads that mapped to each gene for each sample was determined using htseq-count (Anders et al. 2015, *Bioinformatics* 31, 166-169). These counts were then converted to TPM values for each gene and each sample. The inventors then calculated the Spearman correlation coefficient between the co-methylation profiles of all pairs of genes in a similar manner as the co-expression layer, followed by an absolute threshold of 0.95.

CCC Correlation Layer

After filtering the SNP set to remove those with MAF<0.01, the inventors calculated the custom correlation coefficient (CCC) (Climer et al. 2014) between all pairs of remaining SNPs using a Parallel GPU implementation of the CCC (Joubert et al. 2017). The inventors retained correlations from SNP pairs greater than 10 kb apart and with a CCC>=0.7, and then the inventors mapped those SNPs to the genes in which they were located, resulting in gene-gene correlations.

Lines of Evidence Scoring and Network Analysis

The Lines of Evidence (LOE) method calculates a score for every gene by quantifying the connectivity of a given gene to a-priori known genes/phenotypes from the system of interest. These known genes and phenotypes are termed 'anchors' for the purposes of this analysis. Each data layer described above provides one possible line of evidence. For example, if Gene A co-expresses with one or more cell wall anchor genes, then this is counted as one line of evidence for Gene A's involvement in the cell wall. A list of 295 anchor genes was compiled from the literature (Hao and Mohnen, 2014, *Crit. Rev. Biochem. Mol. Biol.* 49, 212-241; Liu et al., 2017, *Sci. Rep.* 7, 1-11; Nakano et al., 2015, *Front. Plant Sci.* 6, 1-18; Rao and Dixon, 2018, *Front. Plant Sci.* 9, 399; Zhong and Ye, 2014, *Plant Cell Physiol.* 56, 195-214). Metabolites that affect cell wall development and composition, such as sugar substrates, lignin precursors, and lignin competitors, were also selected for use as cell wall anchor phenotypes.

To calculate LOE scores for each gene in the *P. trichocarpa* genome, each data layer was represented as a network. Each layer consisted of a list of source entities (cell wall anchor genes and phenotypes, or "anchor nodes"), target entities (potential candidate genes, or "target nodes"), and interactions between them (correlations/associations, or "edges"). From each layer's network, a breadth-first search was used to extract the neighbors of anchor nodes, resulting in a "one-hop" ("1-hop") network for each layer. LOE scores were calculated as per Weighill et al. (2018). Briefly, the LOE breadth score for a gene is the count of the different layers in which that gene has connections to anchor genes/phenotypes. An LOE depth score—the count of all connections to anchor genes/phenotypes across all data layers—was also calculated for each gene. After scoring, the 1-hop networks from all layers were thresholded based on the distribution of LOE breadth scores, then merged to form the LOE network containing cell wall anchor genes and phenotypes and all genes connected to them via one or more layers ("high LOE genes"). All genes in the merged LOE network were ranked based upon breadth and depth scores and genes with previously documented cell-wall-related roles were removed. Networks were visualized and manipulated with Cytoscape 3.6.1 (Shannon et al., 2003, Genome Res. 13, 2498-2504).

Gene Annotation, Functional Enrichment, and Expression Analyses

Functional annotations for *P. trichocarpa* genes were obtained from JGI Phytozome 12 (Goodstein et al., 2011, *Nucleic Acids Res.* 40, D1178--D1186) and MapMan using the Mercator tool (Lohse et al., 2014, *Plant, Cell Environ.* 37, 1250-1258). A number of high LOE genes were not annotated in MapMan or Phytozome. To better understand the potential functions of those genes, protein sequences were extracted from the *P. trichocarpa* v3.1 primary transcript sequence (Tuskan et al., 2006, *Science* (80-.). 313, 1596-1604) available from Phytozome and analyzed using HMMER v3.1b2 (Eddy, 1998) to annotate both Pfam v31.0 (Punta et al., 2011, *Nucleic Acids Res.* 40, D290-D301) and TIGRfam v15.0 (Haft et al., 2001, *Nucleic Acids Res.* 29, 41-43) domains. Domains were thresholded using an independent E-value of 0.001. GO-term enrichment was performed on selected sets of genes using the BinGO Cytoscape app (Maere et al., 2005, *Bioinformatics* 21, 3448-3449) using the Hypergeometric Test as well as Benjamini & Hochberg False Discovery Rate Correction at a significance level of 0.1.

A clustered heatmap of gene expression data was created using the Python (v3.6.2) package seaborn (v0.8.0). Prior to analysis, six samples that were outliers relative to their tissue type and treatment subgroups were removed from the data set. Gene expression was normalized across tissues and genes were clustered using a Euclidean distance metric and Ward clustering method.

To assess orthology for a subset of genes during post-hoc analyses in Section 4.4.1, amino acid sequences containing characteristic PFAM domains were obtained from UniProt (KNOXI: PF03790 per Mukherjee et al., 2009, *Mol. Biol. Evol.* 26, 2775-2794) and reciprocal BLASTp searches were performed against *P. trichocarpa* and *A. thaliana* genomes using NCBI's BLAST with default settings.

Network Validation

Randomizations of Expression and Methylation Data

The inventors assessed whether the coexpression and comethylation networks contain greater biological signal than random networks by performing analyses on multiple randomized expression and methylation datasets. First 100 randomized gene expression data sets were generated by shuffling TPM values within genes across tissues, thereby preserving the observed range of expression for each gene but destroying the associations with tissue samples. A Spearman coexpression matrix was generated for each random dataset and randomly subsampled 100,000 correlation values from each, resulting in a total pool of 10,000,000 random coexpression samples. 10,000,000 random subsamples were collected from the observed coexpression data set and compared the distributions of the observed values to those of the shuffled data sets using the Wilcoxon rank-sum test using the Python package SciPy stats module. The inventors also performed this method with the comethylation data layer.

Functional Validation of LOE Network

To assess whether the observed LOE network captured a greater amount of biological function than random networks, the inventors intersected the observed network as well as 100 randomized LOE networks with a GO-term functional network. The inventors first constructed a functional network from GO Biological Process terms whereby genes that share GO terms are connected and are more likely to share biological function than unconnected genes. GO annotations for *P. trichocarpa* genes were obtained from PlantRegMap (Jin et al., 2017, *Nucleic Acids Res.* 45, D1040-D1045) and removed any term present in over 1000 genes to avoid generating an overly dense network from highly generic functions. Furthermore, the inventors weighted edges with a score inversely proportional to the number of genes with that GO term, such that between genes due to rarer GO terms were considered more functionally valuable than edges due to broader GO terms. If two genes shared multiple GO terms, then the inventors retained only the higher scoring edge. The inventors then generated 100 randomized networks for each input data layer by holding anchor nodes and edges constant and replacing their 1-hop neighbors with gene labels randomly drawn from the genome, thereby ensuring that the size and structure of the randomized networks were comparable to the LOE input networks. For each set of random networks (consisting of one randomized network of each type: comethylation, coexpression, SNP correlation, traditional metabolite-GWAS, and rare variant metabolite-GWAS), LOE scoring and thresholding was performed. Each merged LOE network was then intersected with a GO-term functional network and an intersect score was recorded. The intersect score is calculated by summing the values of the GO-term network edges that are also present in the LOE scored network. The inventors then compared the intersect score of the observed LOE network to the distribution of randomized network intersect scores.

Expression Quantitative Trait Networks eQTN data was utilized as an independent line of evidence for investigating the putative regulatory roles of the PtGRF9 paralogs. RNAseq sequencing data from (Zhang et al., 2018, *New Phytol.* 220, 502-516) were obtained from the NCBI SRA database (SRA numbers: SRP097016-SRP097036). Reads were aligned to the *Populus trichocarpa* v.3.0 reference (Tuskan et al., 2006, *Science.* 313, 1596-1604), using STAR (Dobin et al., 2013, *Bioinformatics* 29, 15-21). Transcript per million (TPM) counts were then obtained for each genotype, resulting in a genotype-transcript matrix. For each gene transcript, outlier values were determined, masking TPM values that exceeded a median absolute deviation from the non-zero median threshold of 5.0. Transcripts that had a non-outlier observed TPM value in more than 20% of the population was retained for further analysis. These expression profiles were then used as phenotypes in a Genome Wide Association Study (GWAS), using EMMAX (Kang et al., 2010, *Nat. Genet.* 42, 348-354). Single nucleotide polymorphisms (SNPs) data, for the same population of *P. trichocarpa* genotypes, was obtained from *Populus* Trichocarpa Genome-Wide Association Study (GWAS) Population SNP Dataset. The SNPs were processed using VCFTOOLS (Danecek et al., 2011, *Bioinformatics* 27, 2156-2158) and PLINK (Purcell et al., 2007, *Am. J. Hum. Genet.* 81, 559-575), selecting for the 90% tranche and a minor allele frequency of 0.01. A hierarchical approach (Peterson et al., 2016, *Genet. Epidemiol.* 40, 45-56) was used to correct for multiple hypotheses bias associated with the number of phenotypes. The procedure involved two rounds of false discovery rate (FDR) corrections, the initial using the Benjamini-Hochberg (Benjamini and Hochberg, 1995, *J. R. Stat. Soc. Ser. B* 57, 289-300) procedure (q1<0.1), followed by the Gavrilov-Benjamini-Sarkar stepdown approach (Gavrilov et al., 2009, *Ann. Stat.* 37, 619-629) (q2<5.1e-4). SNP to phenotype association that passed the respective thresholds were determined to be statistically significant. 1-hop eQTN networks were then created around the PtGRF9 paralogs.

Example 2

Evaluation of Expression and Methylation Data

The Wilcoxon rank-sum test was used to determine whether the distribution of correlation values differed between the observed data set and values from randomized datasets. For both the expression and methylation data sets, the observed distributions were significantly different to random (p<0.01 for both data types). The coexpression data layer was thresholded to exclude correlation values below 0.85, resulting in 16,122 values (0.19%) being retained. In the shuffled data set, only 45 values (or 5.25e-04%) were above the 0.85 threshold. The comethylation data layer was thresholded to exclude correlation values below 0.95, resulting in 87,458 values (0.88%) being retained. In the shuffled data set, only 1,090 values (0.01%) were above the 0.95 threshold.

Construction of LOE Network

The LOE method was used to identify new candidate genes involved in regulating the cell wall in *P. trichocarpa* by jointly probing five different omics data layers. LOE depth scores were calculated for each gene, indicating the number of lines of evidence within each layer connecting that gene to an input set of cell wall anchor genes and metabolites. An LOE breadth score was also calculated for each gene, indicating the number of types of lines of evidence that connected the gene to input cell-wall-related targets. A merged LOE network was created after determining an appropriate LOE breadth score threshold and taking the union of all thresholded input networks. Threshold criteria dictated that candidate genes have a significant association with one or more metabolites in either the traditional or rare variant data layers as well as a total breadth score of three. The inventors required a minimum of one GWAS association for retention in the merged network because metabolite-GWAS associations represent a measurable cell wall phenotype. A breadth score of three was selected in order to prioritize a small set of genes having strong evidence for involvement in cell-wall-related processes, and the distribution of breadth scores exhibits an inflection point at three. These criteria identified a list of 315 "high LOE genes" as potential candidates for involvement in cell-wall-related functions. Seven high LOE genes had a breadth score of four and 308 had a breadth score of three. Overall, high LOE genes were from a variety of functional categories and 80 of these genes were annotated with potential regulatory functions.

Candidate Gene Ranking

To prioritize candidates, the inventors created three ranked tiers to which high LOE genes were assigned (Tier 1 is the highest priority, Tier 3 is the lowest priority). Genes were ranked by 1) breadth score and 2) total depth score minus co-methylation depth score. While the co-expression data vectors contain 64 data points per gene (64 tissues and experimental conditions), the co-methylation data vectors contain only ten data points per gene (ten tissues and experimental conditions), resulting in an increased probability for spurious correlations in the co-methylation data layer. While the distribution of comethylation correlation values was significantly different than random, the shape of the distribution suggests a conservative approach is warranted. In order to avoid upwardly biasing gene rankings, co-methylation data was included in the first stage of the ranking process (overall rank by breadth score) but excluded from the second stage of the ranking process (ranking within breadth score bins by depth score). Genes with an LOE Breadth score of four were included in Tier 1 by default (seven genes). In addition, genes with an LOE Breadth score of three and total depth minus comethylation depth scores of five or greater were included in Tier 1, resulting assignment of 45 genes. Thirty-two genes were assigned to Tier 2 based on a total depth minus comethylation depth score of four. The remaining 238 high LOE genes had total depth minus comethylation depth scores of three or less and were assigned to Tier 3.

Functional Validation of LOE Network

Figure 2A:
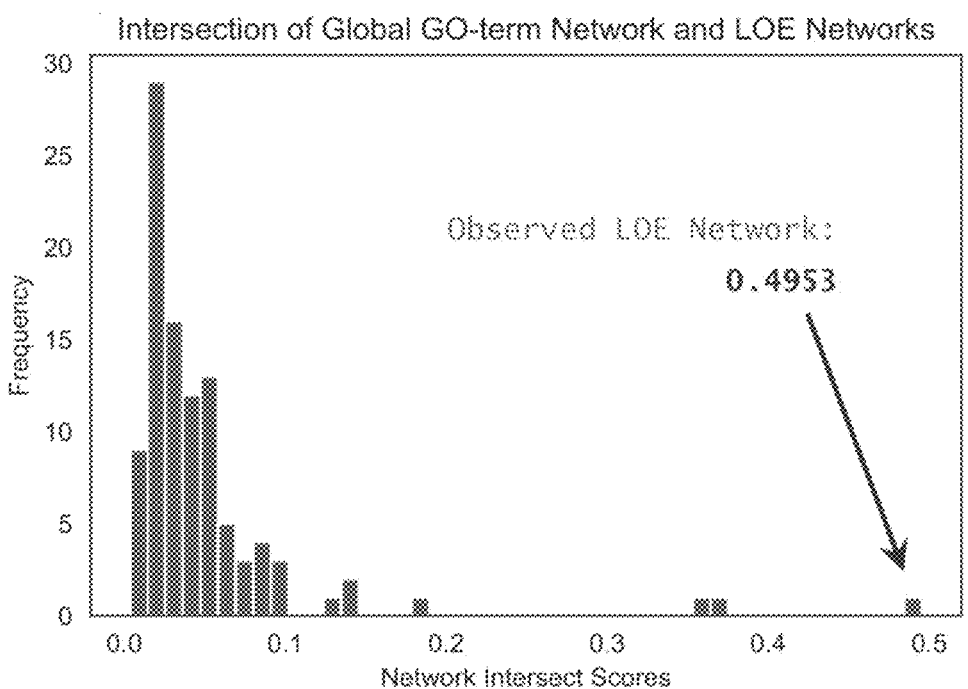
FIGS. 2A-2B. Histograms of network intersect scores calculated by intersecting the observed and randomized LOE networks with GO-term functional networks. (A) Intersection with the global GO-term functional network resulted in a score of 0.4953 for the observed LOE network; intersect scores for randomized networks were ≤0.3701. (B) Intersection with the cell wall-specific GO-term functional network resulted in a score of 0.4806 for the observed LOE network; intersect scores for randomized networks were ≤0.3470.
Figure 2B:
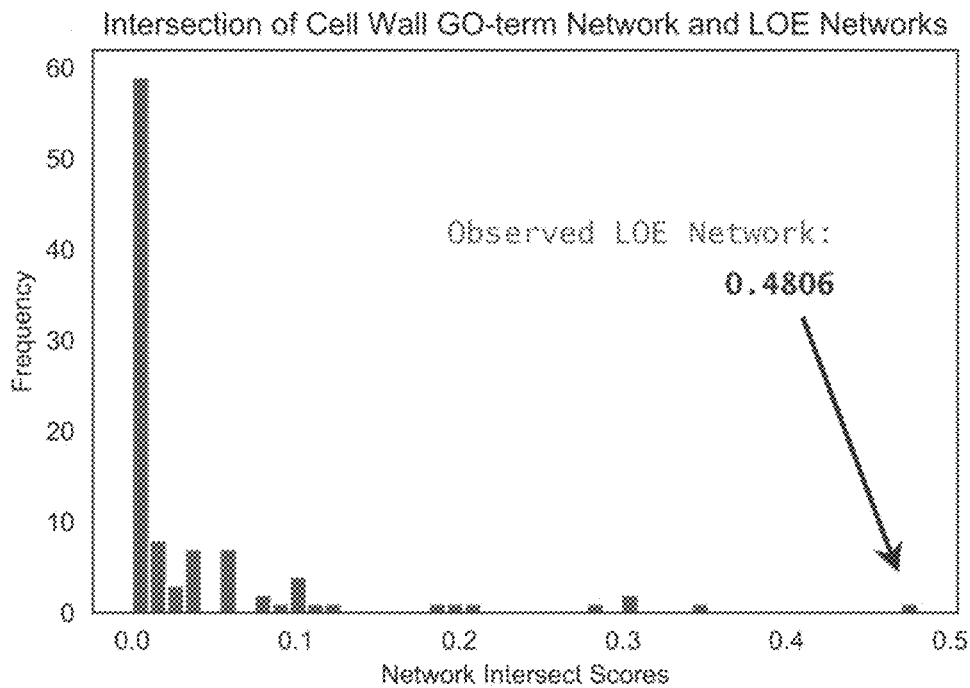

Intersection of the observed thresholded LOE network with the global GO-term functional network resulted in an intersect score of 0.4953, whereas intersect scores for the 100 randomized LOE networks (also thresholded) ranged from 0 to 0.3701 (FIG. 2A). Intersection of the observed LOE network with the cell wall-specific GO-term network resulted in a score of 0.4806; intersect scores for the 100 randomized networks ranged from 0 to 0.3470 (FIG. 2B). These results imply that the observed LOE network captures a greater amount of biological signal than the randomized LOE networks.

Literature Evidence

Recovering genes for which cell-wall-related functions have been previously reported is an important internal validation for the LOE method. The inventors performed an extensive literature review to find evidence of previously validated genes in the results set. Forty-four genes were recovered with previous validation regarding cell-wall-related functions in *P. trichocarpa*, *Arabidopsis*, or other plant species and for which there is evidence of orthology in *P. trichocarpa*. Fifteen of these high LOE genes were also in the anchor gene list. Genes with prior evidence of cell-wall-related functions were removed from the merged LOE network in order to present researchers with "new" candidate genes: fourteen from Tier 1, four from Tier 2, and eleven from Tier 3. However, the literature review process was not as thorough for Tiers 2 or 3, thus it is possible that some of the remaining genes in these tiers have prior connections to cell wall processes. For the remainder of the disclosure, the inventors focus on Tier 1 genes.

A notable example of a high LOE gene with prior evidence of a cell wall regulatory role is IQ-domain 10 calcium-signaling gene PtIQD10 (Potri.011G096500). PtIQD10 has a breadth score of three and a depth score of 48, including rare variant metabolite-GWAS associations with syringin, coniferin, and xylulose, and significant coexpression and comethylation with 41 cell wall anchor genes. The *Arabidopsis* ortholog AtIQD10 (AT3G15050; orthology with PtIQD10 and *P. deltoides* PdIQD10 supported by phylogenetic analysis in Badmi et al., 2018) is differentially expressed in *Arabidopsis* lines overexpressing the transcription factor SECONDARY WALL-ASSOCIATED NAC DOMAIN PROTEIN 2 (AtSND2) (Hussey et al., 2011). Hussey et al. (2011) hypothesize AtIQD10 activates AtSND1 NAC, followed by activation of SND2, MYBs, and cell wall polymerization functions. Consistent with this model, orthologs of these genes are present in the PtIQD10 one-hop neighborhood. Additional evidence has recently been observed in *P. trichocarpa* congeners. An ortholog of PtIQD10 in the *P. alba* x *P. glandulosa* hybrid "84k" is differentially expressed during the transition between primary and secondary growth phases in stems (Li et al., 2017, *J. Plant Physiol.* 213, 1-15). In addition, *P. deltoides* ortholog PdIQD10 has higher expression levels in tension-stressed xylem tissues and secondary walled cells, and RNAi repression of PdIQD10 results in altered phenotypes such as increased cellulose, wall glucose content, plant height, stem count, and stem density (Badmi et al., 2018, *Front. Plant Sci.* 9, 1669; Macaya-Sanz et al., 2017, *Biotechnol. Biofuels* 10, 253). PdIQD10 is coexpressed with secondary cell wall related genes such as SUSY, CESAs, and KOR (Badmi et al., 2018, *Front. Plant Sci.* 9, 1669), orthologs of which are present in the PtIQD10 subnetwork (Potri.018G103900 cellulose synthase/PdCesA7-B I AtCESA7 and Potri.004G059600 PtCESA.2/PdCESA8-B I AtCESA8).

In another example of a high LOE gene with prior evidence of a cell-wall-related role, Porth et al. (2013) found that a SNP in an exostosin family protein gene (Potri.019G044600) involved in xylogalacturonan biosynthesis was correlated with xylose (hemicellulose) content. In yet another example, Pomiès et al. (2017, *BMC Genomics* 18, 300) found a berberine bridge enzyme gene (Potri.011G161500) with orthology to AtEDA28/MEE23 (AT2G34790, shown to play a role in lignin monolignol metabolism) was highly up-regulated 72 hours after mechanical perturbation of stems as plants modified cell wall properties in response. Another example with growing evidence of cell-wall-related regulatory functions is MADS-box transcription factor PtAGL12 (Du et al., 2009, *Plant J.* 60, 1000-1014; Du et al., 2011, *PLoS One* 6, e17458; Weighill et al., 2018, *Front. Energy Res.* 6, 30).

TABLE 1

Highest Priority Candidates for Cell Wall Regulation

| Node # | Gene ID | Arabidopsis gene/domain symbol | Description | Arabidopsis ortholog |
|---|---|---|---|---|
| Regulatory genes | | | | |
| 1 | Potri.008G112300 | | DNA glycosylase superfamily protein | AT1G13635.2 |
| 2 | Potri.001G216000 | EAR1 | ENHANCER OF ABA CO-RECEPTOR 1 | AT5G22090.1 |
| 3 | Potri.013G060500 | ATCRT1 | RING/U-box superfamily protein | AT5G56340.1 |
| 4 | Potri.013G156300 | Shisa | Wnt and FGF inhibitory regulator | |
| 5 | Potri.015G006200 | AtGRF7, GRF7 | growth-regulating factor 7 | AT5G53660.1 |
| 6 | Potri.017G053000 | AMC1, ATMC1, ATMCPB1 | metacaspase 1 | AT1G02170.1 |
| 7 | Potri.018G105600 | YbaB_DNA_bd | YbaB/EbfC DNA-binding family | AT2G24020.1 |
| 8 | Potri.013G093800 | | eukaryotic translation initiation factor SUI1 family protein | AT1G71350.1 |
| 9 | Potri.010G072700 | | RING/U-box superfamily protein | AT5G43420.1 |
| Other genes | | | | |
| | Potri.004G085400 | ATGLN1; 1, ATGSR1, GLN1; 1, GSR 1 | glutamine synthase clone R1 | AT5G37600.1 |
| | Potri.006G256000 | | Phox (PX) domain-containing protein | AT4G32160.1 |
| | Potri.012G093800 | ATNDPK2, NDPK1A, NDPK2 | nucleoside diphosphate kinase 2 | AT5G63310.1 |
| | Potri.010G155600 | | Leucine-rich repeat transmembrane protein kinase | AT1G53440.1 |
| | Potri.001G340400 | SEO_N | SEO_N--Sieve element occlusion N-terminus | |
| | Potri.006G153300 | | N-acetylated-alpha-linked acidic dipeptidase (NAALAD) | AT5G19740.1 |
| | Potri.008G156600 | AST12, SULTR3; 1 | sulfate transporter 3; 1 | AT3G51895.1 |
| | Potri.003G079900 | AW: HRGP | hydroxyproline-rich glycoprotein family protein | AT4G16790.1 |
| | Potri.T135500 | CYCP4; 1 | cyclin p4; 1 | AT2G44740.1 |
| | Potri.018G090300 | AHA1, HA1, OST2, PMA | H(+)-ATPase 1 | AT2G18960.1 |
| | Potri.017G059300 | | serine hydroxymethyltransferase 4 | AT4G13930.1 |
| | Potri.004G059900 | SHM4 | Protein of unknown function DUF1685 | AT2G42760.1 |
| | Potri.016G115200 | | light harvesting complex photosystem II | AT3G08940.2 |
| | Potri.015G063400 | LHCB4.2 | ABC2 homolog 2 | AT3G47740.1 |
| | Potri.019G087700 | ATATH2, ATH2 | somatic embryogenesis receptor-like kinase 1 | AT1G71830.1 |
| | | ATSERK1, SERK1 | | |

TABLE 1-continued

Highest Priority Candidates for Cell Wall Regulation

| Node # | Gene ID | Arabidopsis gene/domain symbol | Description | Arabidopsis ortholog |
|---|---|---|---|---|
| | Potri.007G027400 | | anti-muellerian hormone type-2 receptor | AT3G50685.1 |
| | Potri.005G067000 | | Protein kinase protein with adenine nucleotide alpha hydrolases-like domain | AT1G77280.1 |
| | Potri.001G352200 | ATPUP10, PUP10 | purine permease 10 | AT4G18210.1 |
| | Potri.011G142200 | PSBR | photosystem II subunit R | AT1G79040.1 |
| | Potri.006G060100 | CRR6 | chlororespiratory reduction 6 | AT2G47910.1 |
| | Potri.010G113700 | FAB1C | FORMS APLOID AND BINUCLEATE CELLS 1C | AT1G71010.1 |

Tier 1: Highest Priority Candidates for Cell Wall Regulation

Tier 1 genes have the strongest evidence of involvement in cell wall related processes (Table 1). Of these, nine genes had regulatory annotations (via MapMan, *Arabidopsis* website, or PFAM). While the remaining 21 genes did not have regulatory annotations, the results suggest they play a role in cell wall biosynthesis.

Among Tier 1 regulatory genes, there were a total of eighteen metabolite-GWAS associations, eight of which were rare variant hits. Potri.013G093800 (*Arabidopsis* homolog AT1G71350, a eukaryotic translation initiation factor SUI1 family protein) has the highest number of rare variant metabolite-GWAS associations (six) of any high LOE gene as well as the highest number of total combined GWAS edges (seven). Most Tier 1 regulatory genes share edges with cell wall anchor genes from multiple process categories. On average, Tier 1 genes were connected by multiple edges to four different functional groups, suggesting that Tier 1 genes influence multiple aspects of cell wall biosynthesis. Furthermore, eight Tier 1 regulatory genes shared edges with anchor cell wall transcriptional regulation genes.

Notably, coexpression edges for Tier 1 regulatory genes were either strictly negative for a given gene, or strictly positive, perhaps hinting at the regulatory mechanism of each gene. Two Tier 1 regulatory genes (Potri.015G006200: GROWTH-REGULATING FACTOR 9/PtGRF9 and Potri.018G105600: NUCLEOID-ASSOCIATED PROTEIN YBAB) were negatively coexpressed with cell wall genes and six were positively co-expressed with cell wall genes. The negatively coexpressed genes (Potri.015G006200, Potri.018G105600) did not share any neighbor nodes, however they are both connected to lignin and xylan biosynthesis genes. In contrast, positively coexpressed Tier 1 regulatory genes had a large overlap in neighbor cell wall anchor genes. The overlap was even more pronounced among Potri.008G112300, Potri.001G216000, Potri.013G060500, and Potri.013G156300 despite a complete lack of overlap among metabolite-GWAS edges or MAPMAN functional annotations.

The inventors conducted an in-depth investigation into the Tier 1 regulatory gene PtGRF9 (Potri.015G006200) to assess support for PtGRF9 playing a regulatory role in cell wall biosynthesis.

Example 3: GROWTH-REGULATING FACTOR 9: Putative Master Regulator

The transcription factor gene GROWTH-REGULATING FACTOR 9 (PtGRF9/Potri.015G006200) had a breadth score of three and depth score of seventeen, including thirteen negative coexpression edges (the highest negative coexpression depth score in the analysis). PtGRF9 shared nine edges with lignin biosynthesis genes, four edges with xylan biosynthesis genes, two edges with transcriptional regulation genes, and one edge with a secondary cell wall deposition gene.

The *P. trichocarpa* genome annotation indicates the best-hit *Arabidopsis* match for PtGRF9 is AT5G53660 (growth-regulating factor 7, AtGRF7). To assess support for orthology, the inventors performed reciprocal BLASTp searches of amino acid sequences containing the WRC (PF08879) and QLQ (PF08880) domains from *A. thaliana* and *P. trichocarpa* (obtained from UniProt database) and a phylogenetic analysis. The results support an orthologous relationship between PtGRF9 and AtGRF7, which is consistent with the phylogenetic analysis of Cao et al. (2016, *Front. Plant Sci.* 7, 1-14). While investigating support for orthology between PtGRF9 and AtGRF7, the inventors discovered a second AtGRF7 ortholog in the *P. trichocarpa* genome (Potri.012G022600; hereafter, Potri.015G006200 is referred to as "PtGRF9a" and Potri.012G022600 as "PtGRF9b"). PtGRF9b was not present in the set of high LOE genes because it has a breadth score of 2 and was not associated with any cell wall phenotypes through GWAS analyses. Because PtGRF9b had strong positive coexpression with PtGRF9a and shared edges with many cell wall genes, the inventors included PtGRF9b in further analyses.

The inventors constructed genome-wide 1-hop networks around each PtGRF9 paralog across all data layers to assess the functional annotations of nearest neighbors. PtIQD10 is present in the 1-hop network, along with many other genes with documented roles in cell wall processes. PtGRF9a and PtGRF9b are jointly positively co-expressed with fourteen genes (one of which is a high LOE gene related to cell wall processes) and are jointly negatively co-expressed with 27 genes (including seven cell wall anchor genes and two high LOE genes), implying an overlap in function. However, the bulk of neighbor genes are unique to each paralog, indicating divergence and perhaps specialization for specific tissues and conditions. GO-term functional enrichment analysis of the negative co-expression nodes in the 1-hop network showed significant enrichment for cell wall biological processes, including lignin biosynthesis, xylan biosynthesis and cell wall organization or biogenesis. In addition, the metabolite-GWAS association between PtGRF9a and syringin (a monolignol glucoside) indicated this SNP is associated with an allelic effect on syringin concentration, further implicating PtGRF9a and PtGRF9b as repressors of secondary cell wall formation.

In *Arabidopsis*, AtGRF7 is one of nine members of the GRF family of transcription factors (there are 20 GRF homologs in *P. trichocarpa*) that affect growth via multiple mechanisms (Omidbhakshfard 2015, *Mol. Plant* 8, 998-1010). AtGRF7 has specifically been shown to modulate drought response by repressing DREB2A (Joshi et al., 2016, *Front. Plant Sci.* 7, 1029) which ensures that drought response genes normally activated by DREB2A are not expressed under non-drought conditions, thus avoiding reduced growth. In addition to stress response, GRF genes are involved in regulating cell proliferation and differentiation in the shoot apical meristem (SAM). GRF genes therefore impact the elongation of stems, new leaf initiation, and the size and shape of leaves (Gonzalez et al., 2012, *Trends Plant Sci.* 17, 332-340). The phenotypic penetrance may occur as part of a complex formed with GRF Interacting Factor (GIF1/AN3) proteins (Hoe Kim and Tsukaya, 2015, *J. Exp. Bot.* 66, 6093-6107), where the GRF-GIF complex serves as a transcriptional activator, recruits chromatin remodeling complexes, and regulates the meristematic state of a tissue.

GO-term enrichment analysis of the positive coexpression nodes in the PtGRF9 1-hop network was consistent with roles reported in the literature for GRF genes. The most significantly enriched Biological Process GO terms include specification of axis polarity, shoot system development, shoot system morphogenesis and negative regulation of cell proliferation. Numerous osmotic-stress related genes are also found in the PtGRF9 network (e.g., AHA1/OST2, ERL1, PIP2;2, TIP4;1, and AREB3), reflecting the well-documented relationship between AtGRF7 and drought response. Significant connections between the PtGRF9 paralogs and PtGIF1 or PtDREB2A are not present in the LOE network. On closer inspection of co-expression values across tissues the inventors see that PtGRF9a and PtGIF1 do coexpress strongly in bud and immature leaf, but expression diverges in mature leaf and roots which causes the strength of coexpression to fall just below the 0.85 threshold. The case is less clear for PtDREB2A as it shows little expression in most tissues.

Evidence that the PtGRF9 paralogs play roles in regulating growth, defense, stress response, secondary growth, and cell wall biosynthesis suggest that PtGRF9a and PtGRF9b could be transcriptional co-regulators as described by Xie et al. (2018, *Front. Plant Sci.* 9, 1427), acting as master regulators that direct the global allocation of energy within a plant.

Evidence for Regulation of the Cell Wall by PtGRF9

Figure 3:
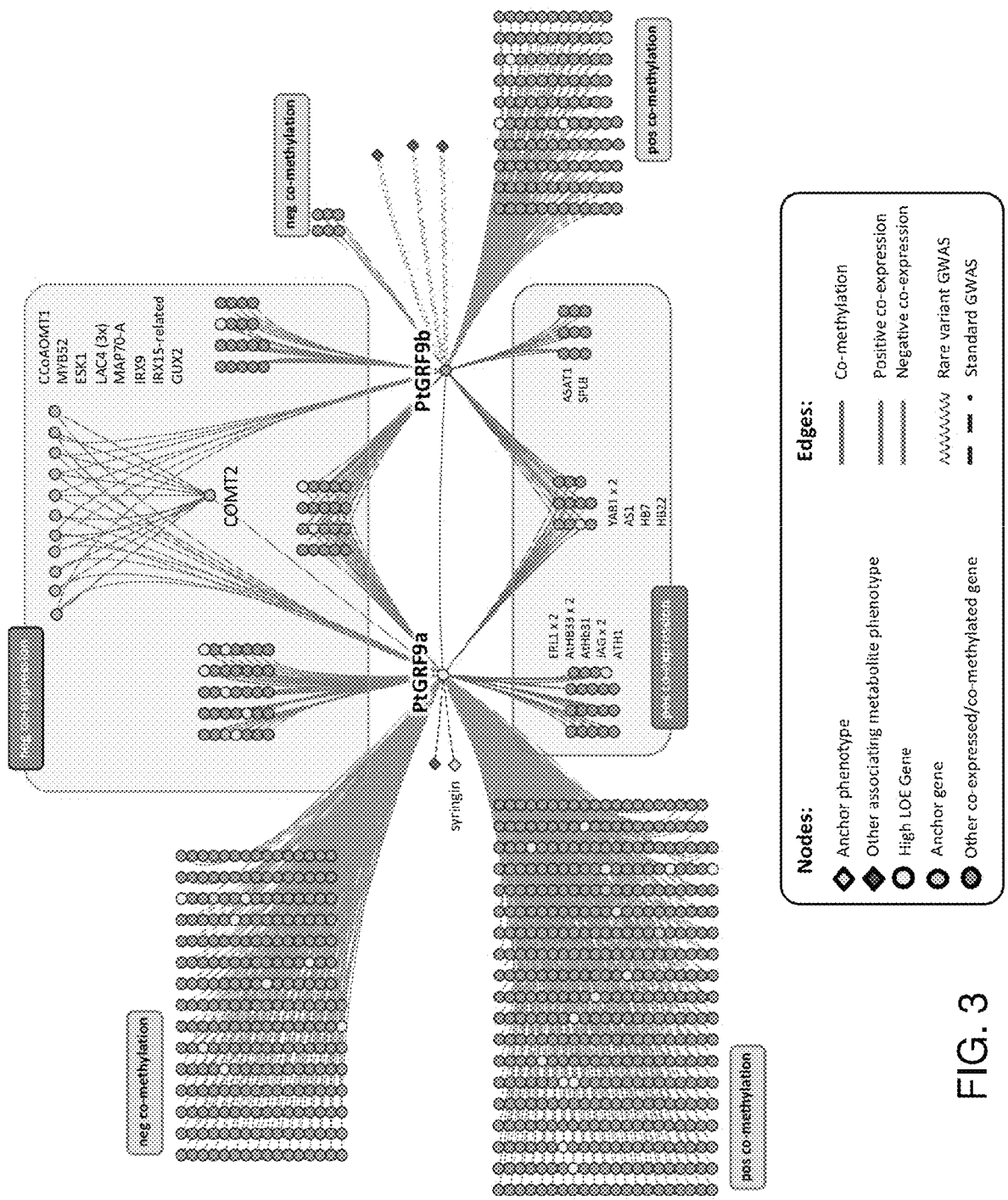
FIG. 3. Genome-wide neighborhood of PtGRF9 paralogs in the global input layer networks. Gene symbols are *Arabidopsis* Best-hit matches.

To date, a role for the GRF family in cell wall regulation has not been reported, though it has been noted that cell proliferation and timing of differentiation must require control or delay of secondary cell wall deposition (Mele et al., 2003, *Genes Dev.* 17, 2088-2093). Barros et al. (2015, *Ann. Bot.* 115, 1053-1074) noted that lignin cannot be removed once deposited, thus, specific regulatory mechanisms are required to control lignin biosynthesis and deposition at specific stages during cell differentiation. The contrasting patterns of coexpression between cell wall biosynthesis and meristematic control in the PtGRF9 1-hop network (FIG. 3) suggest that it could be involved in such a mechanism. Furthermore, the GWAS association with syringin suggests that allelic variation in PtGRF9a in this population may have an additive effect on the amount of sinapyl alcohol stored or released for cell wall lignification.

Knowledge regarding downstream targets of GRF genes is incomplete (see Omidbakhshfard et al., 2015, *Mol. Plant* 8, 998-1010, for a comprehensive review). AtGRF7 has been shown to repress AtDREB2A by binding to the motif TGTCAGG (Kim et al., 2012, *Plant Cell* 24, 3393-3405). Additionally, the central CAG sub-motif is enriched in the promoter of KNOX genes that are targeted by GRFs (Kuijt et al., 2014, *Plant Physiol.* 164, 1952-1966). The inventors searched for the complete TGTCAGG motif in the promoter regions of *Arabidopsis* homologs of the genes that coexpress with PtGRF9a using the online athamap.de tool, revealing two potential AtGRF7 targets in the 1-hop network: caffeoyl coenzyme A O-methyltransferase 1 (AT4G34050 /AtCCoA0MT1) and MADS-box transcription factor AtAGL12 (AT1G71692). Both genes are relevant to the cell wall, and *P. trichocarpa* homologs of these genes are negatively co-expressed with PtGRF9a. To further investigate these genes as potential PtGRF9a targets, the inventors used Analysis of Motif Enrichment (AME) (McLeay and Bailey, 2010, *BMC Bioinformatics* 11(1), 165), but found no evidence for enrichment of the TGTCAGG motif in the 2-kb upstream or CDS regions of PtCCoAOMT (Potri.001G304800 and Potri.009G099800) or PtAGL12 (Potri.013G102600). Manual examination revealed that the TGTCAGG motif appears inexactly in the upstream regions of PtCCoAOMT1 and PtAGL12 (TGTTCAGG in CCoA-OMT 1 Potri.009G099800; TGTCAGC in PtCCoAOMT Potri.001G304800 and PtAGL12). Consistent with the findings of Franco-Zorrilla et al. (2014, *Proc. Natl. Acad. Sci.* 111, 2367-2372), who show that repressor TFs such as PtGRF9a are more likely than activator TFs to bind downstream of a target gene, the inventors found 27 *Populus* genes significantly enriched for TGTCAGG in the 1-kb downstream region, including PtMYB41 (Potri.012G039400, a homolog of AtMYB52), which is negatively coexpressed with PtGRF9a. AtMYB52 is a TF known to induce secondary cell wall biosynthesis genes and its repression reduces secondary wall thickening in fibers (Zhong et al., 2008, *Plant Cell Online* 20, 2763-2782). Furthermore, AtMYB52 overexpression has been linked with drought tolerance (Park et al., 2011, *Mol. Cells* 31, 447-454). Given the established role of AtGRF7 in drought response, repression of PtMYB41 is a potential avenue for PtGRF9a to regulate both lignification and drought tolerance, although further experimental evidence is required.

Figure 4:
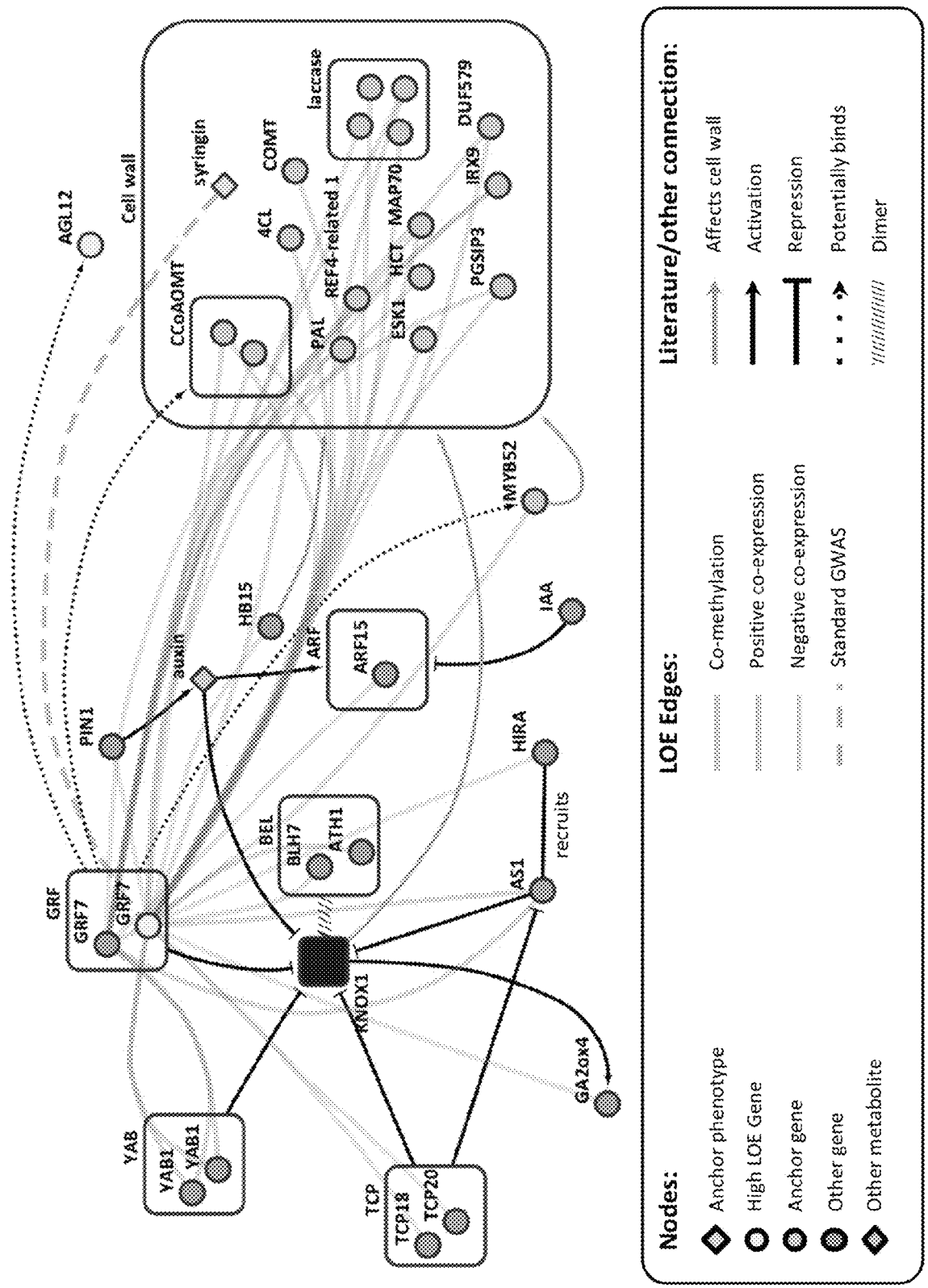
FIG. 4. Literature evidence linking AtGRF7 genes to AtKNOX genes and the cell wall, overlaid on LOE edges from the PtGRF9 subnetwork.

Analysis of the 1-hop network suggests that PtGRF9 also affects cell wall biosynthesis by regulating a host of homeobox genes. Twenty homeobox genes were present in the PtGRF9 network, including PtATHB.12 (Potri.001G188800; homolog of AtHB15/AT1G52150), which has been shown to influence secondary wall formation and cambial production of xylem (Cassan-Wang et al., 2013, *Front. Plant Sci.* 4, 1-14; Schrader, 2004, *Plant Cell Online* 16, 2278-2292), and PtAGL12 (Du et al., 2009, *Plant J.* 60, 1000-1014; Du et al., 2011, *PLoS One* 6, e17458; Weighill et al., 2018, *Front. Energy Res.* 6, 30). There was also indirect evidence in the PtGRF9 network suggesting PtGRF9 interacts with PtKNOX genes. KNOX genes are involved in meristem maintenance and are downregulated to facilitate lateral primordia development and the differentiation of cambium into xylem and phloem (Hay and Tsiantis, 2010, *Development* 137, 3153-3165; Hertzberg et al., 2001, *Proc. Natl. Acad. Sci.* 98, 14732-14737; Schrader, 2004, *Plant Cell Online* 16, 2278-2292). GRF genes are involved in specification of primordia cells and have been shown to repress KNOX genes by forming hairpins in targeted regions (Hoe Kim and Tsukaya, 2015, *J. Exp. Bot.* 66, 6093-6107; Kuijt et al., 2014, *Plant Physiol.* 164, 1952-1966). Interactions between AtGRF7 and KNOX genes have yet to be investigated, but the primary motif of the target sequence by which AtGRF7 binds AtDREB2A was shown to be enriched in several KNOX genes, and experiments in rice, barley, and *Arabidopsis* have confirmed that multiple GRF genes bind these motifs in KNOX genes (Kim et al., 2012, *Plant Cell* 24, 3393-3405; Kuijt et al., 2014, *Plant Physiol.* 164, 1952-1966). The presence of several genes that exclusively or directly interact with KNOX genes in the 1-hop network strongly implies that PtGRF9 proteins influence the cell wall via interactions with the PtKNOX1 genes PtSTM and PtBP, and likely other PtKNOX genes as well (FIG. 4). Although KNOX family genes were not present in the PtGRF9 network, this was likely due to highly tissue-specific expression patterns which the coexpression analysis methods were not designed to detect.

The PtKNOX-associated genes in the PtGRF9 network have documented roles in cell wall and secondary growth phenotypes (FIG. 4). SHOOT-MERISTEMLESS (PtSTM) downregulates gibberellic acid levels by repressing gibberellin 20-oxidase (PtGA20ox) biosynthesis genes and upregulating catabolism genes such as PtGA2ox4 (positively co-methylated with PtGRF9a), which inhibits xylem production (Eriksson et al., 2000, *Nat Biotechnol* 18, 784-788; Jasinski et al., 2005, *Curr. Biol.* 15, 1560-1565). Overexpression of PtSTM/ARBORKNOX1 (PtSTM/PtARK1) in *P. tremula* x *P. alba* has been shown to inhibit differentiation of leaf primordia, elongation of internodes, and differentiation of secondary vascular cells (Groover et al., 2006, *Plant Mol. Biol.* 61,917-932). Counterintuitively, overexpression of PtSTM/PtARK1 in secondary meristems also results in upregulation of some lignin biosynthesis genes and increased lignin content. Long-term transcriptional repression of BREVIPEDICELLUS (AtBP), KNOTTED-like 2 from *A. thaliana* (AtKNAT2) and AtKNAT6 outside the meristem is facilitated by chromatin remodeling carried out by the protein encoded by ASYMMETRIC LEAVES 1 (AtAS1; PtAS1 is positively co-expressed with PtGRF9a and PtGRF9b), which dimerizes with AtAS2 and recruits the histone chaperone protein encoded by AtHIRA (PtHIRA is negatively co-methylated with PtGRF9a) (Guo et al., 2008, *Plant Cell Online* 20, 48-58; Hay and Tsiantis, 2010, *Development* 137, 3153-3165). AS2 is involved in controlling seasonal lignification in spruce, likely through its role in repressing BP (Jokipii-Lukkari et al., 2018, *Plant Physiol.* 176,2851-2870). BP decreases lignin deposition and regulates the localization of lignification by binding the promoters of AtCOMT1, AtCCoAOMT1, laccases, and peroxidases (putative orthologs of which are all negatively co-expressed with PtGRF9a and PtGRF9b) (Mele et al., 2003, *Genes Dev.* 17, 2088-2093). The PtGRF9 network includes many of the cell wall biosynthesis-related genes that Mele et al. (2003) found to be differentially expressed in bp mutants, including five putative orthologs (PAL1, OMT1, two CCoAOMT1 paralogs, PME3, and GH9B5) and an additional 23 genes belonging to the same families as differentially expressed genes in bp mutants (4CL2, five PMEs, KCS19, four peroxidases, four laccases, ERD4, GAUT4, PUB24, MEE23, ERF1-3, and three R2R3 MYBs: MYB52, MYB93, MYB111). Consistent with these observations in *Arabidopsis*, overexpression of AtBP/ARBORKNOX2 (AtBP/AtARK2) in *P. alba* x *P. tremula* results in downregulation of ABNORMAL FLORAL ORGANS (PtAFO/PtYAB1), PIN-FORMED 1 (PtPIN1), PtAGL12 (all negatively co-expressed with PtGRF9a) and PtGA20ox genes, leading to inhibition of cellular differentiation and division and decreases in biomass (Du et al., 2009, *Plant J.* 60, 1000-1014). Furthermore, overexpression of PtBP/PtARK2 results in downregulation of cell wall biosynthesis genes, decreased lignin content, reduced phloem fibers, and reduced secondary xylem in stems.

The inventors did not find a connection between the PtGRF9 genes and cell wall anchor genes KNAT7 (Potri.001G112200, a PtKNOX2 gene) and BEL1-like homeodomain 6 genes (PtBLH6, Potri.004G159300 and Potri.009G120800). These genes have well-documented roles in cell wall regulation (Cassan-Wang et al., 2013, *Front. Plant Sci.* 4, 1-14; Li et al., 2012, *New Phytol.* 194, 102-115). However, the PtGRF9 genes do not appear to be involved in their regulation, perhaps because PtKNOX2 genes are generally more functionally diverse and broadly expressed than PtKNOX1 genes (Furumizu et al., 2015, *PLoS Genet.* 11, 1-24).

PtGRF9 eQTN Network: An Independent Line of Evidence

Figure 5:
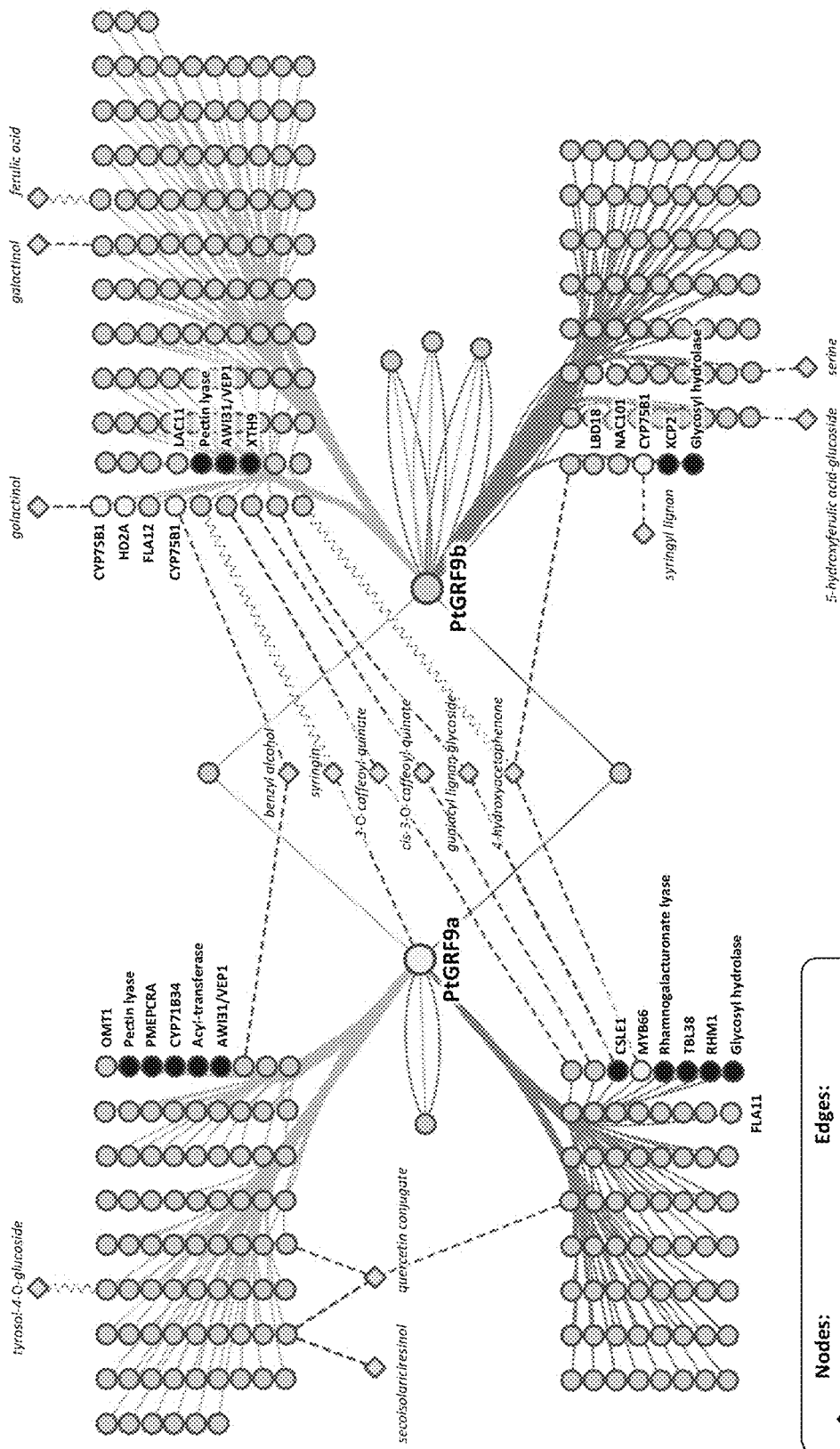
FIG. 5. Two-hop network created by merging a 1-hop eQTN network around the PtGRF9 paralogs and 1-hop metabolite-GWAS networks around anchor metabolites.

As a means of independently evaluating support for the hypothesis that PtGRF9 paralogs regulate cell wall biosynthesis, the inventors constructed 1-hop eQTN networks around PtGRF9a and PtGRF9b (FIG. 5). SNPs in both the PtGRF9a and PtGRF9b 1-hop networks were associated with cell wall expression phenotypes in leaf and xylem tissues, as well as expression phenotypes consistent with the previously documented roles of AtGRF7 and other GRF orthologs in regulating functions such as growth, defense, and stress response. In agreement with the multi-omic 1-hop network described in Section 4.4 (FIG. 3), the eQTN network indicated each paralog has connectivity with cell-wall-related genes affecting multiple facets of cell wall biosynthesis, including transcriptional regulation, cellulose biosynthesis, lignin biosynthesis, xylan biosynthesis, and secondary cell wall deposition. Also consistent with the multi-omic 1-hop network, the eQTN analysis indicated that despite a low degree of topological overlap between the PtGRF9a and PtGRF9b neighborhoods, the paralogs still largely overlap in function.

To gain an understanding of how the PtGRF9 paralogs potentially affect cell wall metabolites, the 1-hop eQTN network was merged with 1-hop anchor metabolite networks generated from traditional and rare variant metabolite-GWAS data layers. Beyond the direct GWAS association of PtGRF9a with syringin, fourteen additional anchor metabolites are present in the 2-hop eQTN to metabolite-GWAS network (FIG. 5), six of which are indirectly associated with both paralogs through various intermediate genes. There appears to be a pattern of segregation regarding metabolite associations between tissue types and PtGRF9 paralogs, perhaps indicating that these genes are diverging to fulfill different tissue-specific regulatory roles.

The extended network analysis pipeline has provided a short list of putative cell wall regulatory genes to the scientific community for experimental validation. The inventors performed an in-depth investigation of the PtGRF9 paralogs, which are particularly promising candidates for regulation of cell wall biosynthesis and secondary growth. Furthermore, the inventors show the PtGRF9 paralogs are potential transcriptional co-regulators that coordinate the flow of energy among growth, defense, stress response, and lignification, in a manner consistent with the hypothesis of Xie et al. (2018, *Front. Plant Sci.* 9, 1427). The ability to manipulate transcriptional co-regulators such as these via genetic engineering and breeding programs would provide a powerful tool for shaping bioenergy crops.

Incorporating a rare variant metabolite-GWAS data layer in the LOE analysis has proven to be a valuable asset in the identification of new candidate genes. Incorporating a genome-wide eQTN (SNP-to-expression-phenotype GWAS) data layer in future analyses would provide greater clarity regarding the mechanisms through which these genes regulate cell-wall-related functions. Furthermore, DNA affinity purification sequencing (DAP-seq) could provide further support for hypothesized transcription factor binding sites, and thus help elucidate relevant transcription factor regulatory networks. Tissue-specific expression analysis across a GWAS population would allow for increased "tissue level resolution" of the regulatory networks. The extended network analysis pipeline will be a valuable tool to integrate these new layers with the previous networks to produce a holistic model of cell wall regulation.

What is claimed is:

1. A genetically modified *Populus* plant, the genetic modification comprising:

inactivation of an endogenous Growth Factor 9 transcription factor (GRF9), [a paralog of GRF9 or a homolog thereof,] wherein the GRF9 comprises an amino acid sequence having at least 90% identity with SEQ ID NO: 1 or SEQ ID NO: 2, and wherein the genetic modification results in an increase in cell wall biosynthesis in the plant [and the genetically modified plant is a *Populus* plant].

2. The genetically modified plant of claim 1, wherein the inactivation of GRF9 is achieved by introducing a nucleic acid inhibitor of GRF9 the plant.

3. The genetically modified plant of claim 2, wherein the nucleic acid inhibitor is selected from the group consisting of an antisense RNA, a small interfering RNA, an RNAi, a microRNA, an artificial microRNA, and a ribozyme.

4. The genetically modified plant of claim 1, wherein the inactivation of GRF9 is achieved by a genome editing method selected from the group consisting of CRISPR/Cas system, Cre/Lox system, TALEN system, ZFNs system and homologous recombination.

5. The genetically modified plant of claim 4, wherein the CRISPR-mediated genome editing comprises introducing into the plant a first nucleic acid encoding a Cas9 nuclease, a second nucleic acid comprising a guide RNA (gRNA), wherein said gRNA is specific to GRF9.

6. A method for increasing a cell wall biosynthesis in a *Populus* plant, comprising:
  inactivating [in a plant] an endogenous Growth Factor 9 transcription factor (GRF9), [a paralog of GRF9 or a homolog thereof,] wherein the GRF9 comprises an amino acid sequence having at least 90% identity with SEQ ID NO: 1 or SEQ ID NO: 2,
  thereby resulting in an increase in cell wall biosynthesis in the plant [, wherein the genetically modified plant is a *Populus* plant].

7. The method of claim 6, wherein the inactivation of GRF9 is achieved by introducing a nucleic acid inhibitor of GRF9 the plant.

8. The method of claim 7, wherein the nucleic acid inhibitor is selected from the group consisting of an antisense RNA, a small interfering RNA, an RNAi, a microRNA, an artificial microRNA, and a ribozyme.

9. The method of claim 6, wherein the inactivation of GRF9 is achieved by a genome editing method selected from the group consisting of CRISPR/Cas system, Cre/Lox system, TALEN system, ZFNs system and homologous recombination.

10. The method of claim 9, wherein the CRISPR-mediated genome editing comprises introducing into the plant a first nucleic acid encoding a Cas9 nuclease, a second nucleic acid comprising a guide RNA (gRNA), wherein said gRNA is specific to GRF9.

11. A method for production of pulp or paper, comprising producing pulp or paper from the genetically modified plant cell or plant tissue [of any one of] claim 1.

12. A method for producing a bioproduct, comprising subjecting the genetically modified plant cell or plant tissue [of any one] of claim 1 to a bioproduct conversion process.

13. The method of claim 12, wherein the bioproduct is selected from the group consisting of a bioenergy product, a biomaterial, a biopharmaceutical and a biocosmetics.

14. The method of claim 13, wherein the bioenergy product is selected from the group consisting of ethanol, butanol and isobutanol.

15. The method of claim 13, wherein the bioenergy product is ethanol and the bioproduct conversion process is an ethanol fermentation process.

16. The method of claim 12, wherein the bioproduct is selected from the group consisting of ethanol, butanol, isobutanol, biodiesel, biogas, bioplastics, biofoams, biorubber, biocomposites, and biofibres.

\* \* \* \* \*

SEQUENCE LISTING

<160> NUMBER OF SEQ ID NOS: 5

<210> SEQ ID NO 1
<211> LENGTH: 435
<212> TYPE: PRT
<213> ORGANISM: Populus balsamifera subsp. trichocarpa

<400> SEQUENCE: 1

```
Met Ser Lys Ser Gln Val Trp Cys Gly Leu Thr Asn Thr Val Ile Phe
1               5                   10                  15

Phe Leu Pro Ser Ser Gly Gly Asn Met Ala Ala Ser Leu Gly Phe Pro
            20                  25                  30

Phe Thr Asn Ala Gln Trp Asn Glu Leu Glu Arg Gln Ala Met Ile Tyr
        35                  40                  45

Lys Tyr Met Val Ser Ser Asn His Val Pro Pro His Leu Leu Ile Pro
    50                  55                  60

Thr Pro Leu Met Gly Asn Gly Leu Asp Val Arg Phe Thr Lys Arg Ala
65                  70                  75                  80

Asp Leu Glu Pro Gly Arg Cys Arg Arg Thr Asp Gly Lys Lys Trp Arg
                85                  90                  95

Cys Ser Arg Asp Val Ala Pro Asp Lys Lys Tyr Cys Glu Arg His Met
            100                 105                 110

His Arg Gly Arg Pro Arg Ser Arg Lys His Val Glu Leu Asn Thr Ser
        115                 120                 125

Ser Asn Ser Asn Ser Asn Lys Lys Ser Arg His Asn Pro Ser Ile Cys
    130                 135                 140

Thr Glu Ser Pro Val Thr Val Ala Ile Ser Asn Pro Thr Ile Asn Asn
145                 150                 155                 160

Asn Asn Ser Ser Ser Ala Ser His Asp His Phe Val Gly Thr Met Pro
                165                 170                 175

Gln Pro Tyr Ile Gln Thr Pro Val Phe Val Asn Lys Thr Ser Glu Lys
            180                 185                 190

Ile Ala Thr Phe Asp Ala Asn Gly Ala Phe Gly Ser Thr Tyr Lys Glu
        195                 200                 205

Pro Arg Ser Phe Asp Trp Met Leu Lys Gly Gly Thr Gly Pro Ile Val
    210                 215                 220

Thr Asn Asp Gln Gln Trp Pro His Leu Val His Thr Glu Ile Gly Leu
225                 230                 235                 240

Ala Thr Glu Gly Ser Phe Asn Asn Ala Ser Val Leu Lys Gln His Tyr
                245                 250                 255

Arg Glu Glu Ser Leu Asn Leu Asn Ser Tyr Gly Asn Leu Asn Ala Arg
            260                 265                 270

Glu Asp Gln His Arg Ser Gln Tyr Ser Leu Phe Leu Asp Gly Ala Pro
        275                 280                 285

Arg Ser Tyr Ile Asp Ala Trp Ser Asn Asp Ala Asn Ser Gly Asn Thr
    290                 295                 300

Ser Ser Val Ser Ser Asp Gly Lys Leu Pro Leu Ser Pro Leu Ser Leu
```

```
            305                 310                 315                 320
Ser Met Gly Gly Asn Arg Ser Val Asp Asp Glu Met Gly Gln Ile Gln
                325                 330                 335

Met Gly Leu Gly Leu Ile Lys Pro Asp Gln Asn Gln Glu Cys Gly Gly
                340                 345                 350

Asp Thr Ser Ser Thr Pro Gly Gly Pro Leu Ala Glu Val Leu Gln Leu
                355                 360                 365

Arg Thr Val Asn Ile Asn Thr Gly Thr Asn Gln Ser Ser Ser Val Ile
                370                 375                 380

Glu Asn Gly Asp Ser Ile Cys Pro Pro Ala Thr Arg Val Ser Ser Pro
385                 390                 395                 400

Ser Glu Val Leu Gln Lys Thr His Ala Ser Leu Ser Asp Ser Ser Gly
                405                 410                 415

Asn Arg Val Gln His Leu Pro Val Gln Gly Pro Asn Leu Lys Leu Pro
                420                 425                 430

Cys Phe Gly
        435

<210> SEQ ID NO 2
<211> LENGTH: 535
<212> TYPE: PRT
<213> ORGANISM: Populus balsamifera subsp. trichocarpa

<400> SEQUENCE: 2

Met Met Thr Thr Asp Asp Gly Leu Asn Val Ser Asn Lys Val Ala Lys
1               5                   10                  15

Glu Ile Asn Thr Thr Ser Ser Ile Ser Asn Val Asp Phe Gly Val Lys
                20                  25                  30

Leu His Gln Pro Ile Asp His His Gln Ser Phe Pro Ser Ser Thr Pro
            35                  40                  45

Met Met Val Pro His Val Asn His His Arg Pro Met Phe Asp Asn Gly
        50                  55                  60

Pro Thr Ser Ser Cys Asp Arg Asn Lys Ser Leu Met Asn Tyr Ile Ser
65                  70                  75                  80

Asp Arg Ile Tyr Arg Val Ala Ala Gly Ala Thr Ser Gly Gly Ala
                85                  90                  95

Val Gly Val Arg Asn Leu Gln Pro Phe Asp Ile Ser Glu Thr Ser Ile
                100                 105                 110

Ser Thr Ala Ala Ser Ala Phe Arg Ser Pro Gly Gly Asn Met Ala Ala
            115                 120                 125

Ser Leu Gly Phe Pro Phe Thr Asn Thr Gln Trp Lys Glu Leu Glu Arg
        130                 135                 140

Gln Ala Met Ile Tyr Asn Tyr Ile Thr Ala Ser Val Pro Val Pro Pro
145                 150                 155                 160

Gln Phe Leu Ile Pro Thr Pro Met Gly Asn Gly Leu Asn Val Arg Phe
                165                 170                 175

Ser Asn Gly Ala Asp Leu Glu Pro Gly Arg Cys Arg Arg Thr Asp Gly
            180                 185                 190

Lys Lys Trp Arg Cys Ser Arg Asp Val Ala Pro Asp Gln Lys Tyr Cys
        195                 200                 205

Glu Arg His Met His Arg Gly Arg Pro Arg Ser Arg Lys His Val Glu
        210                 215                 220

Leu Asn Ala Ser Asn Asn Asn Lys Lys Asn Arg His Asn Pro Ala
225                 230                 235                 240
```

```
Ile Cys Pro Glu Ala Pro Val Thr Val Ala Ile Ser Lys Pro Thr Ile
                245                 250                 255
Asn Asn Ser Asn Ser Gly Ser Ala Ser His Asp Gln Phe Phe Gly Pro
            260                 265                 270
Met Pro Gln Pro Tyr Ile Gln Thr Pro Val Phe Val Asn Lys Thr Ser
        275                 280                 285
Glu Lys Thr Ser Thr Tyr Asp Val Asn Gly Ala Tyr Gly Ser Thr Phe
    290                 295                 300
Lys Glu Pro Arg Ser Leu Asp Trp Met Leu Lys Gly Glu Ala Gly Pro
305                 310                 315                 320
Ile Ala Lys Asn Asp Gln Gln Trp Pro His Leu Val His Lys Glu Ile
                325                 330                 335
Glu Leu Ala Thr Glu Gly Ser Phe Asn Ser Ala Ser Val Leu Lys Gln
            340                 345                 350
His Tyr Gln Gly Glu Ser Leu Asn Leu Asn Ser Phe Gly Asn Phe Asn
        355                 360                 365
Ala Arg Glu Asp Gln Ser Asn Gln Tyr Ser Leu Phe Leu Asp Glu
    370                 375                 380
Ala Pro Arg Ser Phe Ile Asp Ala Trp Ser Asn Asp Ala Ile Ser Arg
385                 390                 395                 400
Asn Thr Ser Ser Val Ser Ser Asp Gly Lys Leu His Leu Ser Pro Leu
                405                 410                 415
Ser Leu Ser Met Gly Ser Asn Arg Ser Thr Asp Asp Glu Met Gly Gln
            420                 425                 430
Ile Gln Met Gly Leu Gly Leu Ile Lys Ser Asp Arg Asn Glu Glu Cys
        435                 440                 445
Gly Asn Thr Ser Ser Ala Pro Gly Gly Pro Leu Ala Glu Val Leu Gln
    450                 455                 460
Leu Arg Thr Ser Asn Thr Thr Gly Thr Asn Gln Ser Ser Ser Met Met
465                 470                 475                 480
Glu Asn Gly Asp Ser Ile Ser Pro Pro Ala Thr Thr Val Ser Ser Pro
                485                 490                 495
Ser Gly Val Leu Gln Lys Thr Leu Ala Ser Phe Ser Asp Ser Ser Gly
            500                 505                 510
Asn Ser Ser Pro Thr Leu Ala Ser Ser Arg Thr Lys Pro Glu Ile Ala
        515                 520                 525
Met Leu Trp Leu Asn Gln Gly
    530                 535

<210> SEQ ID NO 3
<211> LENGTH: 247
<212> TYPE: PRT
<213> ORGANISM: Populus balsamifera subsp. trichocarpa

<400> SEQUENCE: 3

Met Ala Ala Asn Gly Glu Glu Gln Gln Thr Gln Ala Gly Arg His Gln
1               5                   10                  15
Glu Val Gly His Lys Ser Leu Leu Gln Ser Asp Ala Leu Tyr Gln Tyr
            20                  25                  30
Ile Leu Glu Thr Ser Val Tyr Pro Arg Glu Pro Glu Cys Met Lys Glu
        35                  40                  45
Leu Arg Glu Leu Thr Ala Lys His Pro Trp Asn Ile Met Thr Thr Ser
    50                  55                  60
Ala Asp Glu Gly Gln Phe Leu Asn Met Leu Leu Lys Leu Ile Asn Ala
65                  70                  75                  80
```

```
Lys Asn Thr Met Glu Ile Gly Val Phe Thr Gly Tyr Ser Leu Leu Ala
                85                  90                  95

Thr Ala Leu Ala Ile Pro Glu Asp Gly Lys Ile Leu Ala Met Asp Ile
            100                 105                 110

Asn Arg Glu Asn Tyr Glu Leu Gly Leu Pro Val Ile Gln Lys Ala Gly
        115                 120                 125

Leu Glu His Lys Ile Glu Phe Lys Glu Gly Pro Ala Leu Pro Val Leu
    130                 135                 140

Asp Gln Met Ile Glu Asp Gly Lys Tyr His Gly Thr Tyr Asp Phe Ile
145                 150                 155                 160

Phe Val Asp Ala Asp Lys Asp Asn Tyr Ile Asn Tyr His Lys Arg Leu
                165                 170                 175

Ile Glu Leu Val Lys Val Gly Gly Leu Ile Gly Tyr Asp Asn Thr Leu
            180                 185                 190

Trp Asn Gly Ser Val Val Ala Pro Ala Asp Ala Pro Met Arg Lys Tyr
        195                 200                 205

Val Arg Tyr Tyr Arg Asp Phe Val Leu Glu Leu Asn Lys Ala Leu Ala
    210                 215                 220

Ala Asp Pro Arg Ile Glu Ile Cys Met Leu Pro Val Gly Asp Gly Ile
225                 230                 235                 240

Thr Leu Cys Arg Arg Ile Lys
                245

<210> SEQ ID NO 4
<211> LENGTH: 247
<212> TYPE: PRT
<213> ORGANISM: Populus balsamifera subsp. trichocarpa

<400> SEQUENCE: 4

Met Ala Thr Asn Gly Glu Gln Gln Ser Gln Ala Gly Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Cys Met Lys Glu
        35                  40                  45

Leu Arg Glu Val Thr Ala Lys His Pro Trp Asn Ile Met Thr Thr Ser
    50                  55                  60

Ala Asp Glu Gly Gln Phe Leu Asn Met Leu Leu Lys Leu Val Asn Ala
65                  70                  75                  80

Lys Asn Thr Met Glu Ile Gly Val Tyr Thr Gly Tyr Ser Leu Leu Ala
                85                  90                  95

Thr Ala Leu Ala Ile Pro Glu Asp Gly Lys Ile Leu Ala Met Asp Ile
            100                 105                 110

Asn Arg Glu Asn Tyr Glu Leu Gly Leu Pro Val Ile Gln Lys Ala Gly
        115                 120                 125

Val Ala His Lys Ile Asp Phe Lys Glu Gly Pro Ala Leu Pro Val Leu
    130                 135                 140

Asp Gln Met Ile Glu Asp Gly Lys Cys His Gly Ser Phe Asp Phe Ile
145                 150                 155                 160

Phe Val Asp Ala Asp Lys Asp Asn Tyr Ile Asn Tyr His Lys Arg Leu
                165                 170                 175

Ile Glu Leu Val Lys Val Gly Gly Leu Ile Gly Tyr Asp Asn Thr Leu
            180                 185                 190

Trp Asn Gly Ser Val Val Ala Pro Pro Asp Ala Pro Met Arg Lys Tyr
```

```
                    195                 200                 205
Val Arg Tyr Tyr Arg Asp Phe Val Leu Glu Leu Asn Lys Ala Leu Ala
    210                 215                 220

Ala Asp Pro Arg Ile Glu Ile Cys Met Leu Pro Val Gly Asp Gly Ile
225                 230                 235                 240

Thr Leu Cys Arg Arg Ile Gln
                245

<210> SEQ ID NO 5
<211> LENGTH: 243
<212> TYPE: PRT
<213> ORGANISM: Populus balsamifera subsp. trichocarpa

<400> SEQUENCE: 5

Met Cys Thr Arg Gly His Trp Arg Pro Ala Glu Asp Glu Lys Leu Lys
1               5                   10                  15

Glu Leu Val Glu Lys Tyr Gly Pro His Asn Trp Asn Ala Ile Ala Glu
                20                  25                  30

Lys Leu Gln Gly Arg Ser Gly Lys Ser Cys Arg Leu Arg Trp Phe Asn
            35                  40                  45

Gln Leu Asp Pro Arg Ile Asn Arg Ser Pro Phe Thr Glu Glu Glu Glu
    50                  55                  60

Glu Arg Leu Leu Ala Ser His Arg Ile His Gly Asn Arg Trp Ala Ile
65                  70                  75                  80

Ile Ala Arg Phe Phe Pro Gly Arg Thr Asp Asn Ala Val Lys Asn His
                85                  90                  95

Trp His Val Ile Met Ala Arg Arg Tyr Arg Glu Arg Ser Arg Leu His
                100                 105                 110

Ala Lys Arg Ala Ala Gln Thr Leu Val Asn Asp Asn Lys Leu Ser Ser
            115                 120                 125

Lys Gln Asp His Met His Met Asp Cys Glu Thr Arg Asn Phe Ser Ser
    130                 135                 140

Phe Ser Lys Lys Tyr Cys Glu Lys Tyr Gly Gln Tyr Pro Met Val Thr
145                 150                 155                 160

His Ser Tyr Leu Pro Ala Phe Cys Lys Glu Phe Tyr Asn Glu Asp Pro
                165                 170                 175

Ser His Cys Glu Asp Gln Ser Arg Pro Ile Glu Phe Tyr Asp Phe Leu
            180                 185                 190

Gln Val Asn Thr Asp Ser Asn Lys Ser Glu Val Ile Asp Asn Ala Arg
    195                 200                 205

Arg Asp Asp Glu Glu Val Asp Gln Gln Glu Ala Leu Glu Asn Asn Gln
                210                 215                 220

Ser Lys Ala Asp Val Pro Phe Ile Asp Phe Phe Ser Val Asn Gly Lys
225                 230                 235                 240

Ser Ser Ser
```